(12) United States Patent  
Marks et al.

(10) Patent No.: US 8,754,188 B2
(45) Date of Patent: Jun. 17, 2014

(54) SEMICONDUCTING COMPOUNDS AND DEVICES INCORPORATING SAME

(75) Inventors: Tobin J. Marks, Evanston, IL (US); Antonio Facchetti, Chicago, IL (US); Pierre-Luc Boudreault, Evanston, IL (US); Hiroyuki Miyauchi, Yokkaichi (JP)

(73) Assignee: Northwestern University, Evanston, IL (US)

( * ) Notice: Subject to any disclaimer, the term of this patent is extended or adjusted under 35 U.S.C. 154(b) by 53 days.

(21) Appl. No.: 13/429,005

(22) Filed: Mar. 23, 2012

(65) Prior Publication Data

US 2012/0264906 A1    Oct. 18, 2012

Related U.S. Application Data

(60) Provisional application No. 61/467,015, filed on Mar. 24, 2011, provisional application No. 61/466,801, filed on May 9, 2011.

(51) Int. Cl.
*C08G 75/00* (2006.01)

(52) U.S. Cl.
USPC ............................ 528/377; 528/90; 549/42

(58) Field of Classification Search
USPC ............................ 528/477, 377, 90; 549/42
See application file for complete search history.

(56) References Cited

U.S. PATENT DOCUMENTS

| | | | |
|---|---|---|---|
| 5,936,259 A | 8/1999 | Hatz et al. | |
| 7,605,394 B2 | 10/2009 | Marks et al. | |
| 7,678,463 B2 | 3/2010 | Marks et al. | |
| 7,981,989 B2 | 7/2011 | Yan | |
| 2010/0032655 A1 | 2/2010 | Takimiya et al. | |
| 2011/0224445 A1* | 9/2011 | Takimiya | ................... 549/42 |

FOREIGN PATENT DOCUMENTS

| | | |
|---|---|---|
| EP | 1524286 | 4/2005 |
| EP | 1916250 | 4/2008 |
| EP | 2034537 | 3/2009 |
| JP | 2006216814 | 8/2006 |
| JP | 2010180151 | 8/2010 |
| WO | 2008002660 | 1/2008 |
| WO | 2010058692 | 5/2010 |

OTHER PUBLICATIONS

Shiraishi, K., et al., "New pi-conjugated polymers constituted of dialkoxybenzodithiophene units: synthesis and electronic properties," Synthetic Metals, 2002, 130, 139-147.*

International Search Report from PCT/US2012/030382 issued Dec. 3, 2012.

Tamayo, Arnold Bernarte; Tantiwiwat, Mananya; Walker, Bright; and Nguyen, Thuc-Quyen, "Design, Synthesis, and Self-Assembly of Oligothiophene Derivatives with a Diketopyrrolopyrrole Core", J. Phys. Chem. C 2008, 112, 15543-15552.

(Continued)

*Primary Examiner* — Mark Eashoo
*Assistant Examiner* — Nicholas Hill
(74) *Attorney, Agent, or Firm* — Reinhart Boerner Van Deuren s.c.

(57) ABSTRACT

Disclosed are molecular and polymeric compounds having desirable properties as semiconducting materials. Such compounds can exhibit desirable electronic properties and possess processing advantages including solution-processability and/or good stability. Organic transistor and photovoltaic devices incorporating the present compounds as the active layer exhibit good device performance.

14 Claims, 6 Drawing Sheets

(56) References Cited

OTHER PUBLICATIONS

Coropceanu, Veaceslav; Kwon, Ohyun; Wex, Brigitte; Kaafarani, Bilal R.; Gruhn, Nadine E.; Durivage, Jason C.; Neckers, Douglas C.; and Bredas, Jean-Luc, "Vibronic Coupling in Organic Semiconductors: The Case of Fused Polycyclic Benzene-Thiophene Structures", Chem. Eur. J. 2006, 12, 2073-2080.

Umeda, Rui; Fukuda, Hiroshi; Miki, Koji; Rahman, S. M. Abdur; Sonoda, Motohiro; Tobe, Yoshito, "Formation of naphthodithiophene isomers by flash vacuum pyrolysis of 1,6-di(2-thienyl)- and 1,6-di(3-thienyl)-1,5-hexadien-3-ynes", Science Direct, C.R. Chimie 12 (2009) 378-384.

Goto, Hiromasa and Akagi, Kazuo, "Optically Active Conjugated Polymers Prepared from Achiral Monomers by Polycondensation in a Chirmal Nematic Solvent", Angew. Chem. Int. Ed. 2005, 44, 4322-4328.

Osaka, Itaru; Sauve, Genevieve; Zhang, Rui; Kowalewski, Tomasz; and McCullough, Richard D., "Novel Thiophene-Thiazolothiazole Copolymers for Organic Field-Effect Transistors", Adv. Mater. 2007, 19, 4160-4165.

Wheeler, Alvin S. and Ergle, David R., "Naphthol Studies I. The Bromination of 1,5-Dihydroxynaphthalene", Journal of the American Chemcial Society (1930), 52, 4872-80.

\* cited by examiner

SEMICONDUCTING COMPOUNDS AND DEVICES INCORPORATING SAME

CROSS REFERENCE TO RELATED APPLICATIONS

This application claims priority to and the benefit of U.S. Provisional Patent Application Ser. No. 61/467,015 filed on Mar. 24, 2011 and U.S. Provisional Patent Application Ser. No. 61/466,801 filed on May 9, 2011, the disclosure of each of which is incorporated by reference herein in its entirety.

STATEMENT REGARDING FEDERALLY SPONSORED RESEARCH OR DEVELOPMENT

This invention was made with government support under Grant No. DE-SC0001059 awarded by the U.S. Department of Energy. The government has certain rights in the invention.

BACKGROUND

A new generation of electronic, optical or optoelectronic devices such as organic thin film transistors (OTFTs), organic light-emitting transistors (OLETs), organic light-emitting diodes (OLEDs), or organic photovoltaics (OPVs) are fabricated using organic semiconductors as their active components. To be commercially relevant, these organic semiconductor-based devices should be processable in a cost-effective manner.

Several p- and n-channel organic semiconductors have achieved acceptable device performance. For example, OTFTs based on acenes and oligothiophenes (p-channel) and perylenes (n-channel) exhibit carrier mobilities ($\mu$'s)>0.5 $cm^2/V\cdot s$ in ambient conditions. Furthermore, a variety of polymeric and molecular semiconductor materials incorporating one or more fused thiophene rings have been synthesized and/or proposed as organic semiconductor building blocks, which includes naphthodithiophene rings reported in Umeda, R., et al., Comptes Rendus Chimie (2009), 12(3-4), 378-384; Coropceanu, V., et al., Chemistry-A European Journal (2006), 12(7), 2073-2080; Takahashi, T., et al., JP 2010180151 A; Takimiya, K., et al., WO 2010058692 A1; Katakura, T., et al., JP 2006216814 A; and Katz, H. E., et al., U.S. Pat. No. 5,936,259 A. Although many of these materials exhibit acceptable carrier mobilities, improved processability is required for commercial feasibility. For example, pentacene exhibits high hole mobility >5 $cm^2/V\cdot s$ with its highly crystalline nature, but cannot be processed via printing methodologies due to its insolubility.

Accordingly, the art desires new polymeric or molecular semiconductors, particularly those having well-balanced semiconducting properties and processing properties.

SUMMARY

In light of the foregoing, the present teachings provide polymeric and molecular semiconductors that can address various deficiencies and shortcoming of the prior art, including those outlined above. Also provided are associated devices and related methods for the preparation and use of these semiconductors. The present semiconductors can exhibit properties such as excellent charge transport characteristics, low temperature processability, satisfactory solubility in common solvents, and processing versatility (e.g., printability). As a result, field effect devices such as thin film transistors that incorporate one or more of the present semiconductors can exhibit high performance, for example, demonstrating one or more of large hole mobility, large electron mobility, low threshold voltages, and high current on-off ratios. Similarly, other organic semiconductor-based devices such as OPVs, OETs, and OLEDs can be fabricated efficiently using the organic semiconductor materials described herein.

Generally, the present teachings provide polymeric and molecular semiconducting compounds comprising a 5,10-dialkoxynaphtho[2,3-b:6,7-b']dithiophene (NDT) moiety. For example, various embodiments of the present compounds can be represented by:

formula (I)

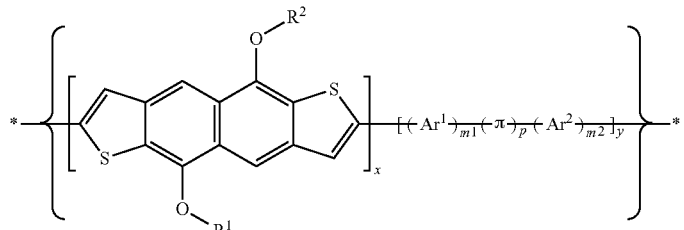

or formula (II)

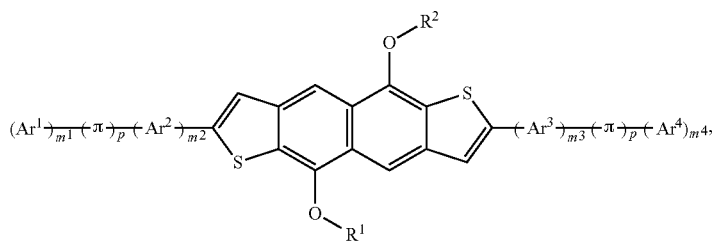

wherein $R^1$, $R^2$, $Ar^1$, $Ar^2$, $Ar^3$, $Ar^4$, $\pi$, $m^1$, $m^2$, $m^3$, $m^4$, p, x and y are as defined herein.

The present teachings also provide methods of preparing such polymeric and molecular semiconductor materials, as well as various compositions, composites, and devices that incorporate the polymeric and molecular semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
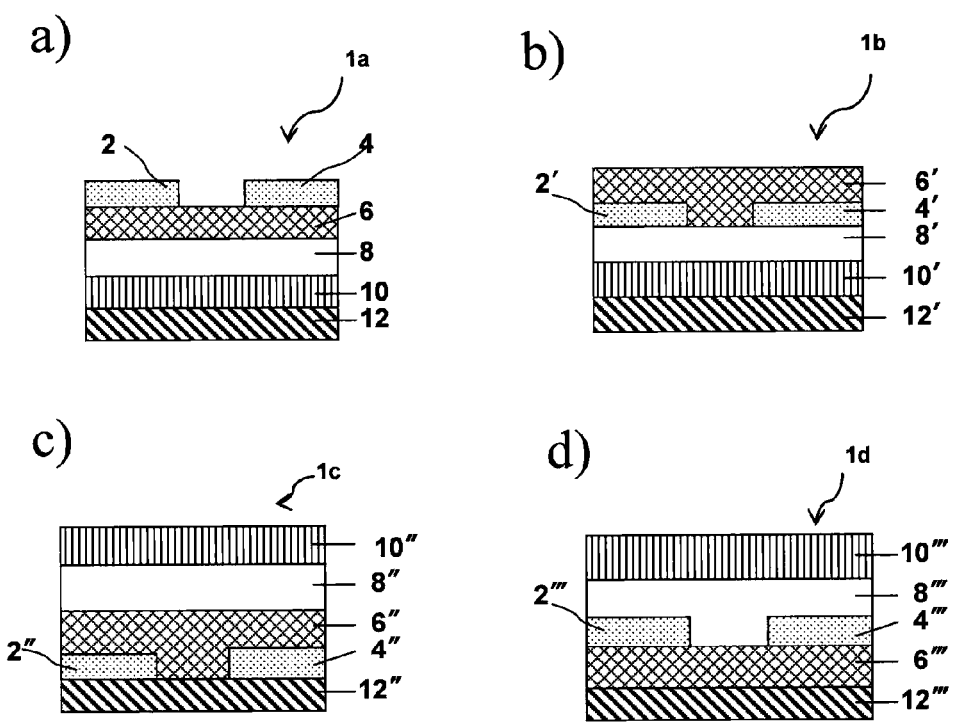
FIG. 1 illustrates four different configurations of thin film transistors: bottom-gate top contact (a), bottom-gate bottom-contact (b), top-gate bottom-contact (c), and top-gate top-contact (d); each of which can be used to incorporate compounds of the present teachings.

The present teachings provide organic semiconductor materials that include polymeric and molecular semiconductors and associated compositions, composites, and/or devices. Organic semiconductor materials of the present teachings can exhibit semiconducting behavior such as high carrier mobility and/or good current modulation characteristics in a field-effect device, light absorption/charge separation in a photovoltaic device, and/or charge transport/recombination/light emission in a light-emitting device. In addition, the present materials can possess certain processing advantages such as solution-processability. The materials of the present teachings can be used to fabricate various organic electronic articles, structures and devices, including field-effect transistors, unipolar circuitries, complementary circuitries, photovoltaic devices, and light emitting devices.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "polymeric compound" (or "polymer") refers to a molecule including a plurality of one or more repeating units connected by covalent chemical bonds. As used herein, a repeating unit in a polymer must repeat itself at least twice (as specified by its degree of polymerization) in the polymer. A polymer can be represented by the general formula:

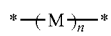

wherein M is the repeating unit or monomer. The degree of polymerization (n) can range from 2 to greater than 10,000, typically in the range from 5 to about 10,000. The polymer can have only one type of repeating unit as well as two or more types of different repeating units. When a polymer has only one type of repeating unit, it can be referred to as a homopolymer. When a polymer has two or more types of different repeating units, the term "copolymer" can be used instead. The polymer can be linear or branched. Branched polymers can include dendritic polymers, such as dendronized polymers, hyperbranched polymers, brush polymers (also called bottle-brushes), and the like. Unless specified otherwise, the assembly of the repeating units in a copolymer can be head-to-tail, head-to-head, or tail-to-tail. In addition, unless specified otherwise, the copolymer can be a random copolymer, an alternating copolymer, or a block copolymer. For example, the general formula:

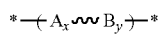

can be used to represent a copolymer of A and B having x mole fraction of A and y mole fraction of B in the copolymer, where the manner in which comonomers A and B is repeated can be alternating, random, regiorandom, regioregular, or in blocks.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can be optionally substituted as described herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein. For example, an —O-haloalkyl group is considered within the definition of "alkoxy" as used herein.

As used herein, "alkylthio" refers to an —S-alkyl group (which, in some cases, can be expressed as —$S(O)_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is defined as a divalent alky group that can be optionally substituted as described herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

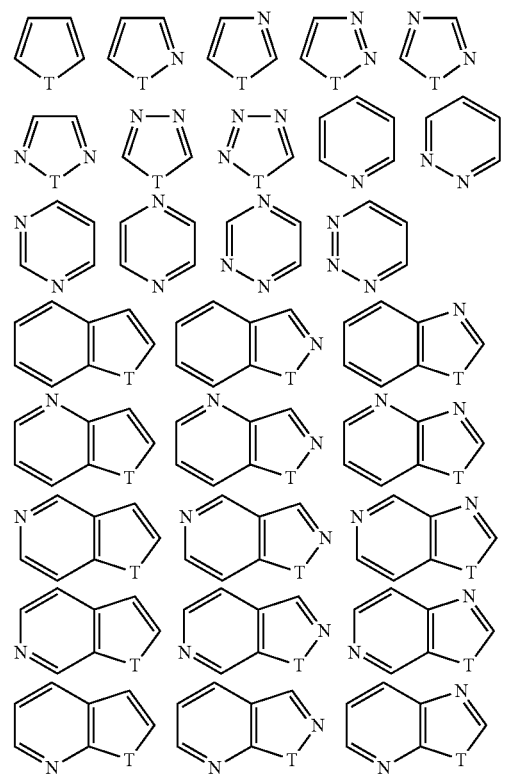

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group), a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^0)_2{}^+$, —$N(R^0)_3{}^+$, —$SO_3H$, —$SO_2R^0$, —$SO_3R^0$, —$SO_2NHR^0$, —$SO_2N(R^0)_2$, —COOH, —$COR^0$, —$COOR^0$, —$CONHR^0$, —$CON(R^0)_2$, $C_{1-40}$ haloalkyl groups, $C_{6-14}$ aryl groups, and 5-14 membered electron-poor heteroaryl groups; where $R^0$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —$NO_2$, —CN, —NC, —$S(R^0)_2{}^+$, —$N(R^0)_3{}^+$, —$SO_3H$, —$SO_2R^0$, —$SO_3R^0$, —$SO_2NHR^0$, —$SO_2N(R^0)_2$, —COOH, —$COR^0$, —$COOR^0$, —$CONHR^0$, and —$CON(R^0)_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —$OR^0$, —$NH_2$, —$NHR^0$, —$N(R^0)_2$, and 5-14 membered electron-rich heteroaryl groups, where $R^0$ is a $C_{1-20}$ alkyl group, a $C_{2-20}$ alkenyl group, a $C_{2-20}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current or charge carriers. In some embodiments, when a p-type semiconductor material is deposited on a substrate, it can provide a hole mobility in excess of about $10^{-5}$ cm²/Vs. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current or charge carriers. In some embodiments, when an n-type semiconductor material is deposited on a substrate, it can provide an electron mobility in excess of about $10^{-5}$ cm²/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

As used herein, fill factor (FF) is the ratio (given as a percentage) of the actual maximum obtainable power, ($P_m$ or $V_{mp}*J_{mp}$), to the theoretical (not actually obtainable) power, ($J_{sc} \times V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from absorbed light to electrical energy. The PCE of a solar cell can be calculated by dividing the maximum power point ($P_m$) by the input light irradiance (E, in W/m²) under standard test conditions (STC) and the surface area of the solar cell ($A_c$ in m²). STC typically refers to a temperature of 25° C. and an irradiance of 1000 W/m² with an air mass 1.5 (AM 1.5) spectrum.

As used herein, a component (such as a thin film layer) can be considered "photoactive" if it contains one or more compounds that can absorb photons to produce excitons for the generation of a photocurrent.

Throughout the specification, structures may or may not be presented with chemical names. Where any question arises as to nomenclature, the structure prevails.

In one aspect, the present teachings relate to polymeric semiconducting compounds, as well as the use of these compounds in electronic, optoelectronic, or optical devices. The polymeric compounds (or polymers) according to the present teachings generally can be represented by formula (I):

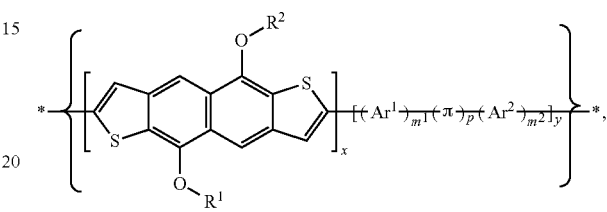

wherein:

$R^1$ and $R^2$ independently are a $C_{1-20}$ alkyl group or a $C_{1-20}$ haloalkyl group;

$Ar^1$ and $Ar^2$ independently are an optionally substituted $C_{6-14}$ aryl group or an optionally substituted 5-14 membered heteroaryl group;

π is an optionally substituted polycyclic aryl or heteroaryl group;

$m^1$ and $m^2$ independently are 0, 1, 2, 3 or 4;

p is 0 or 1;

x and y are real numbers representing mole fractions, wherein $0<x\leq1$, $0\leq y<1$, and the sum of x and y is about 1; and the polymeric compound has a degree of polymerization (n) in the range of 5 to 10,000.

To illustrate, each of $R^1$ and $R^2$ independently can be a linear or branched $C_{1-40}$ alkyl groups such as methyl, ethyl, n-propyl, isopropyl, n-butyl, iso-butyl, sec-butyl, tert-butyl, n-pentyl, iso-pentyl, neo-pentyl, n-hexyl, n-dodecyl,

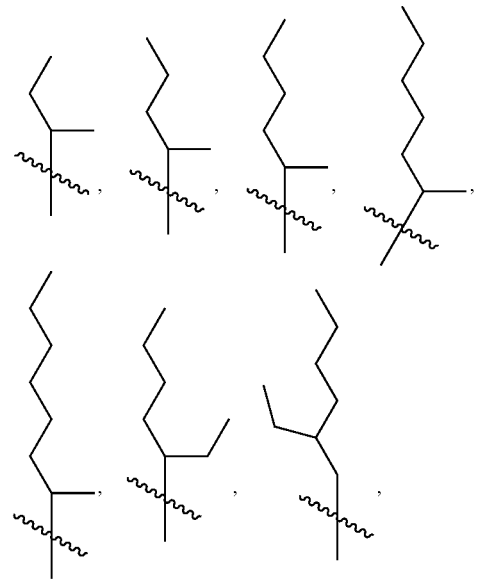

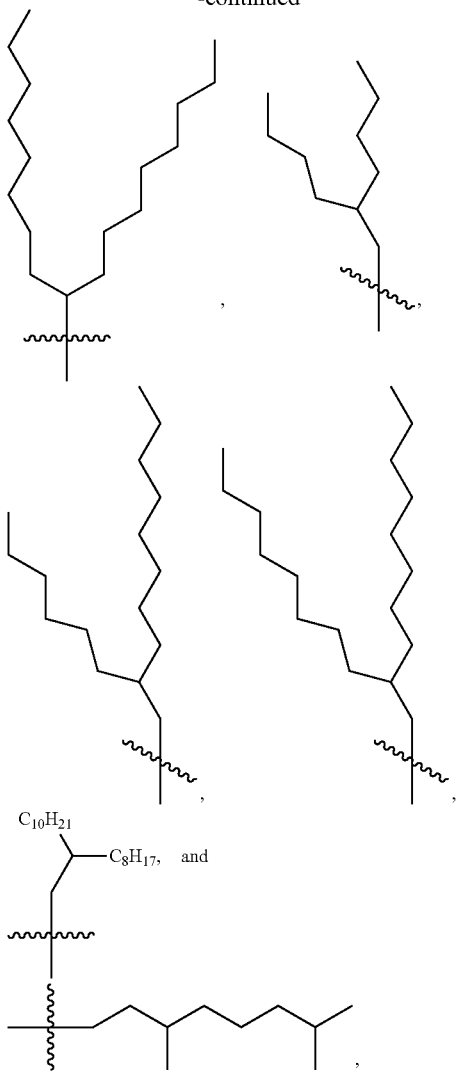

or a linear or branched $C_{1-40}$ haloalkyl groups where one or more hydrogen atoms in, for example, the $C_{1-40}$ alkyl groups shown above, are replaced by a halogen such as F.

Examples of $Ar^1$ and $Ar^2$ include various conjugated monocyclic and polycyclic moieties which can be optionally substituted as described herein. For example, each of $Ar^1$ and $Ar^2$ optionally can be substituted with 1-6 $R^d$ groups, where $R^d$, at each occurrence, independently is selected from a) halogen, b) —CN, c) —$NO_2$, d) —$N(R^e)_2$, e) oxo, f) —OH, g) =$C(R^f)_2$, h) —$C(O)R^e$, i) —$C(O)OR^e$, j) —$C(O)N(R^e)_2$, k) —SH, l) —$S(O)_2$—$R^e$, m) —$S(O)_2OR^e$, n) —$(OCH_2CH_2)_tOR^e$, o) —$(OCF_2CF_2)_tOR^e$, p) —$(OCH_2CF_2)_tOR^e$, q) —$(OCF_2CH_2)_tOR^e$, r) —$(CH_2CH_2O)_tR^e$, s) —$(CF_2CF_2O)_tR^e$, t) —$(CH_2CF_2O)_tR^e$, u) —$(CF_2CH_2O)_tR^e$, v) a $C_{1-40}$ alkyl group, w) a $C_{2-40}$ alkenyl group, x) a $C_{2-40}$ alkynyl group, y) a $C_{1-40}$ alkoxy group, z) a $C_{1-40}$ alkylthio group, aa) a $C_{1-40}$ haloalkyl group, ab) a —Y—$C_{3-10}$ cycloalkyl group, ac) a —Y—$C_{6-14}$ aryl group, ad) a —Y—$C_{6-14}$ haloaryl group, ae) a —Y-3-12 membered cycloheteroalkyl group, and af) a —Y-5-14 membered heteroaryl group, wherein each of the $C_{1-40}$ alkyl group, the $C_{2-40}$ alkenyl group, the $C_{2-40}$ alkynyl group, the $C_{1-40}$ alkoxy group, the $C_{1-40}$ alkylthio group, the $C_{1-40}$ haloalkyl group, the $C_{3-10}$ cycloalkyl group, the $C_{6-14}$ aryl group, the $C_{6-14}$ haloaryl group, the 3-12 membered cycloheteroalkyl group, and the 5-14 membered heteroaryl group is optionally substituted with 1-4 $R^f$ groups;

$R^e$, at each occurrence, independently is selected from H, a $C_{1-40}$ alkyl group, a $C_{1-40}$ haloalkyl group, and a —Y—$C_{6-14}$ aryl group;

$R^f$, at each occurrence, independently is selected from a) halogen, b) —CN, c) —$NO_2$, d) oxo, e) —OH, f) —$NH_2$, g) —$NH(C_{1-20}$ alkyl), h) —$N(C_{1-20}$ alkyl)$_2$, i) —$N(C_{1-20}$ alkyl)-$C_{6-14}$ aryl, j) —$N(C_{6-14}$ aryl)$_2$, k) —$S(O)_wH$, l) —$S(O)$, $C_{1-20}$ alkyl, m) —$S(O)_2OH$, n) —$S(O)_2$—$OC_{1-20}$ alkyl, o) —$S(O)_2$—$OC_{6-14}$ aryl, p) —CHO, q) —$C(O)$—$C_{1-20}$ alkyl, r) —$C(O)$—$C_{6-14}$ aryl, s) —$C(O)OH$, t) —$C(O)$—$OC_{1-20}$ alkyl, u) —$C(O)$—$OC_{6-14}$ aryl, v) —$C(O)NH_2$, w) —$C(O)NH$—$C_{1-20}$ alkyl, x) —$C(O)N(C_{1-20}$ alkyl)$_2$, y) —$C(O)NH$—$C_{6-14}$ aryl, z) —$C(O)N(C_{1-20}$ alkyl)-$C_{6-14}$ aryl, aa) —$C(O)N(C_{6-14}$ aryl)$_2$, ab) —$C(S)NH_2$, ac) —$C(S)NH$—$C_{1-20}$ alkyl, ad) —$C(S)N(C_{1-20}$ alkyl)$_2$, ae) —$C(S)N(C_{6-14}$ aryl)$_2$, af) —$C(S)N(C_{1-20}$ alkyl)-$C_{6-14}$ aryl, ag) —$C(S)NH$—$C_{6-14}$ aryl, ah) —$S(O)_wNH_2$, ai) —$S(O)_wNH(C_{1-20}$ alkyl), aj) —$S(O)_wN(C_{1-20}$ alkyl)$_2$, ak) —$S(O)_wNH(C_{6-14}$ aryl), al) —$S(O)_wN(C_{1-20}$ alkyl)-$C_{6-14}$ aryl, am) —$S(O)_wN(C_{6-14}$ aryl)$_2$, an) —$SiH_3$, ao) —$SiH(C_{1-20}$ alkyl)$_2$, ap) —$SiH_2(C_{1-20}$ alkyl), aq) —$Si(C_{1-20}$ alkyl)$_3$, ar) a $C_{1-20}$ alkyl group, as) a $C_{2-20}$ alkenyl group, at) a $C_{2-20}$ alkynyl group, au) a $C_{1-20}$ alkoxy group, av) a $C_{1-20}$ alkylthio group, aw) a $C_{1-20}$ haloalkyl group, ax) a $C_{3-10}$ cycloalkyl group, ay) a $C_{6-14}$ aryl group, az) a $C_{6-14}$ haloaryl group, ba) a 3-12 membered cycloheteroalkyl group, or bb) a 5-14 membered heteroaryl group;

Y, at each occurrence, independently is selected from a divalent $C_{1-10}$ alkyl group, a divalent $C_{1-10}$ haloalkyl group, and a covalent bond;

t is 1, 2, 3, 4, 5, 6, 7, 8, 9 or 10; and w, at each occurrence, independently is 0, 1, or 2.

Examples of monocyclic (hetero)aryl groups include a phenyl group or a 5- or 6-membered heteroaryl group such as a pyrrolyl group, a furyl group, a thienyl group, a pyridyl group, a pyrimidyl group, a pyridazinyl group, a pyrazinyl group, a triazolyl group, a tetrazolyl group, a pyrazolyl group, an imidazolyl group, an isothiazolyl group, a thiazolyl group, and a thiadiazolyl group. For example, at least one of the $Ar^1$ and/or the $Ar^2$ groups can include at least one 5-membered heteroaryl group that includes at least one sulfur ring atom. Examples of such sulfur-containing 5-membered heteroaryl group include a thienyl group, a thiazolyl group, an isothiazolyl group, and a thiadiazolyl group, each of which optionally can be substituted with 1-4 $R^3$ groups, where $R^3$, at each occurrence, independently can be selected from a halogen, CN, oxo, =$C(CN)_2$, a $C_{1-40}$ alkyl group, a $C_{1-40}$ haloalkyl group, a $C_{1-40}$ alkoxy group, and a $C_{1-40}$ alkylthio group.

Examples of bicyclic 8-14 membered (hetero)aryl groups include a naphthyl group and various bicyclic (e.g., 5-5 or 5-6) heteroaryl moieties that include at least one sulfur ring atom. Examples of such sulfur-containing bicyclic heteroaryl moieties include a thienothiophenyl group (e.g., a thieno[3, 2-b]thiophenyl group or a thieno[2,3-b]thiophenyl group), a benzothienyl group, a benzothiazolyl group, a benzisothiazolyl group, and a benzothiadiazolyl group, each of which optionally can be substituted with 1-4 $R^3$ groups, where $R^3$, at each occurrence, independently can be selected from a halogen, CN, oxo, =$C(CN)_2$, a $C_{1-40}$ alkyl group, a $C_{1-40}$ haloalkyl group, a $C_{1-40}$ alkoxy group, and a $C_{1-40}$ alkylthio group.

By way of example, $Ar^1$ and $Ar^2$, at each occurrence, independently can be selected from:

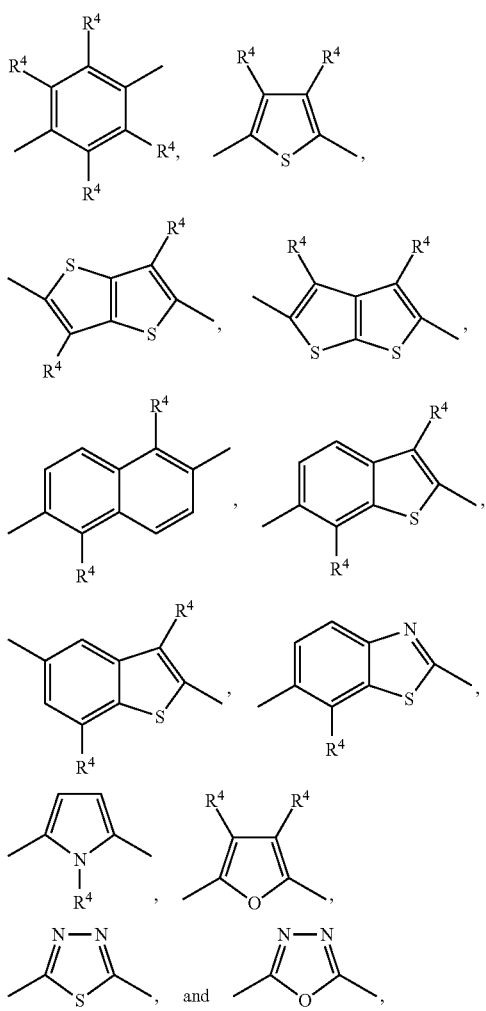

where $R^4$, at each occurrence, independently can be H or $R^3$, and $R^3$ can be selected from a halogen, CN, oxo, =$C(CN)_2$, a $C_{1-40}$ alkyl group, a $C_{1-40}$ haloalkyl group, a $C_{1-40}$ alkoxy group, and a $C_{1-40}$ alkylthio group.

In various embodiments, at least p and/or at least one of $m^1$ and $m^2$ is not 0. For example, in certain embodiments, each of $m^1$ and $m^2$ can be 1, and $Ar^1$ and $Ar^2$, at each occurrence, independently can be an optionally substituted thienyl group or an optionally substituted bicyclic heteroaryl group comprising a thienyl group fused with a 5-membered heteroaryl group. In particular embodiments, the present polymers can have the formula:

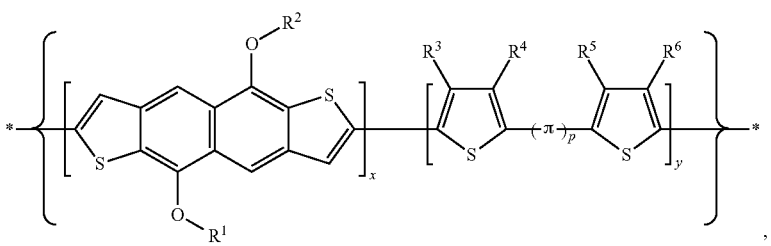

wherein:
$R^3$, $R^4$, $R^5$, and $R^6$ independently are selected from H and $R^7$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and
$R^1$, $R^2$, $\pi$, p, x and y are as defined herein.

In certain embodiments, p can be 0. An example of such embodiments can be a polymer having the formula:

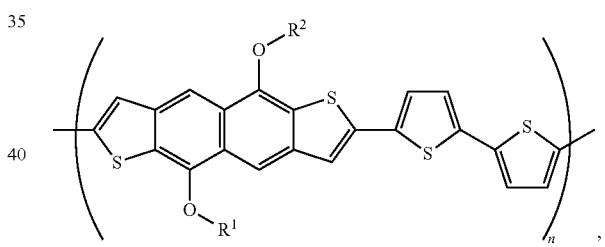

where $R^1$ and $R^2$ independently can be a $C_{1-20}$ alkyl group; and n is an integer ranging from 5 to 10,000. Another example of such embodiments can be a polymer having the formula:

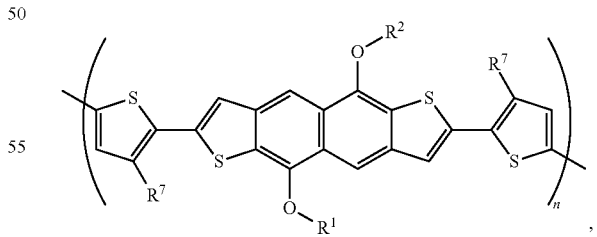

where $R^1$ and $R^2$ independently can be a $C_{1-20}$ alkyl group, where each $R^7$ is selected from a halogen, CN, a $C_{1-20}$ alkyl group, a $C_{1-20}$ haloalkyl group, a $C_{1-20}$ alkoxy group, and a $C_{1-20}$ alkylthio group; and n is an integer ranging from 5 to 10,000.

In certain embodiments, p can be 1. Examples of such embodiments can include polymers having the formula:

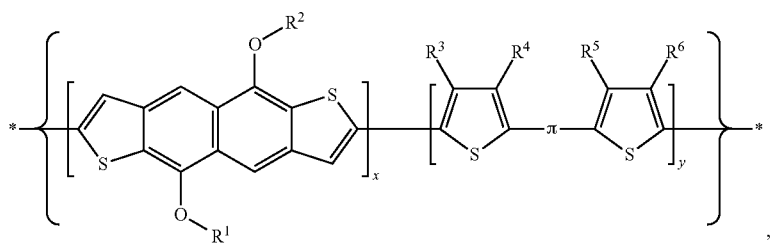

wherein π is an optionally substituted heteroaryl group. For example, π can be a polycyclic $C_{8-24}$ aryl group or a polycyclic 8-24 membered heteroaryl group, where each of these groups can be optionally substituted with 1-6 $R^d$ groups, where $R^d$ is as defined herein. In certain embodiments, π can include at least one electron-withdrawing group. In certain embodiments, π can include one or more solubilizing groups. For example, π can include one or more solubilizing groups selected from a $C_{1-40}$ alkyl group, a $C_{1-40}$ alkoxy group, a $C_{1-40}$ alkylthio group, a $C_{1-40}$ haloalkyl group, —(OCH$_2$CH$_2$)$_t$OR$^e$, —(OCF$_2$CF$_2$)$_t$OR$^e$, —(OCH$_2$CF$_2$)$_t$OR$^e$, —(OCF$_2$CH$_2$)$_t$OR$^e$, —(CH$_2$CH$_2$O)$_t$—R$^e$, —(CF$_2$CF$_2$O)$_t$R$^e$, —(CH$_2$CF$_2$O)$_t$R$^e$, or —(CF$_2$CH$_2$O)$_t$R$^e$; where t is 1, 2, 3, 4, 5, 6, 7, 8, 9 or 10; and $R^e$ is a $C_{1-20}$ alkyl group or a $C_{1-20}$ haloalkyl group.

In certain embodiments, π can be an optionally substituted heteroaryl group represented by a formula selected from:

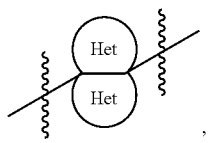

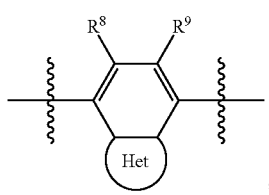

, and

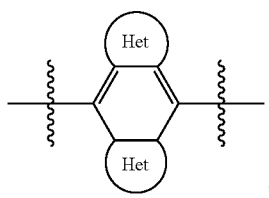

;

wherein Het, at each occurrence, is a monocyclic moiety including at least one heteroatom in its ring and optionally substituted with 1-2 $R^{10}$ groups, wherein $R^8$, $R^9$, and $R^{10}$ independently can be H or $R^2$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and $R^1$, $R^2$, x and y are as defined herein.

In particular embodiments, it can be selected from:

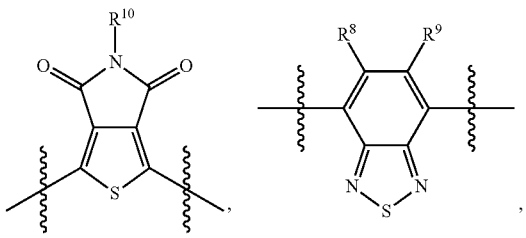

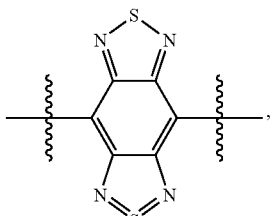

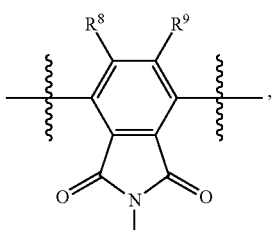

, and

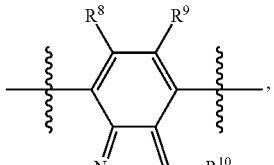

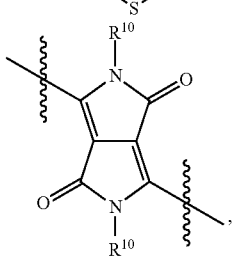

where $R^8$, $R^9$, and $R^{10}$ independently can be selected from H, halogen, CN, a $C_{1-20}$ alkyl group, a $C_{1-20}$ haloalkyl group, a $C_{1-20}$ alkoxy group, and a $C_{1-20}$ alkylthio group.

To illustrate, an example of a polymer having the formula:

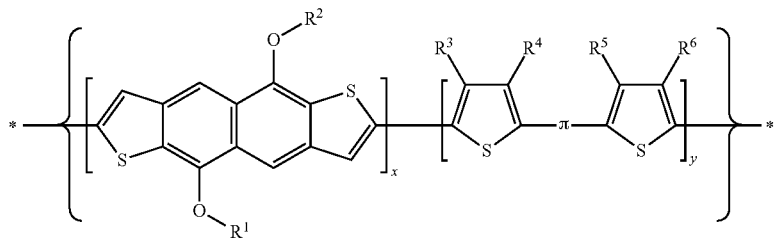

can be

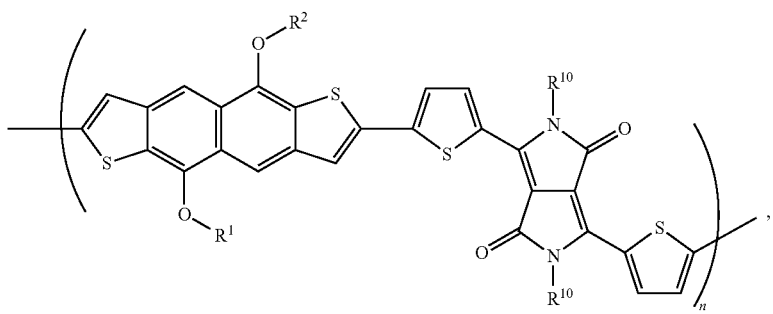

where $R^1$, $R^2$ and $R^{10}$ independently can be a $C_{1-20}$ alkyl group, and n is an integer ranging from 5 to 10,000.

In some embodiments, polymers according to the present teachings can have the formula:

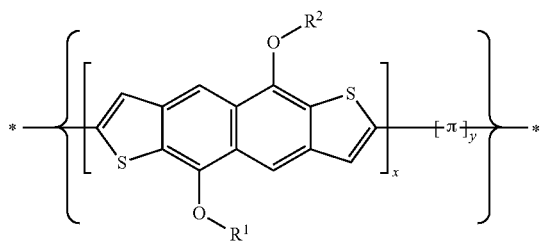

wherein π is as defined herein. For example, π can be an optionally substituted heteroaryl group represented by a formula selected from:

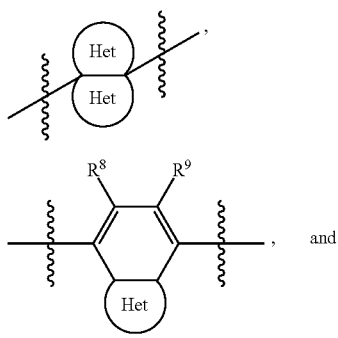

-continued

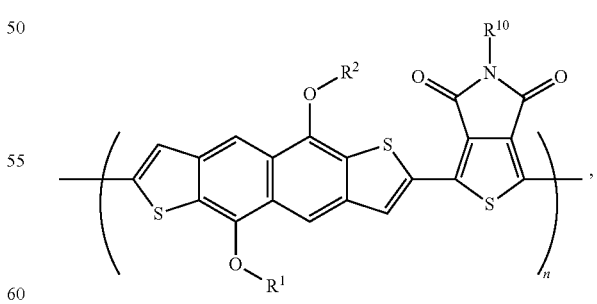

wherein Het, at each occurrence, is a monocyclic moiety including at least one heteroatom in its ring and optionally substituted with 1-2 $R^{10}$ groups, wherein $R^8$, $R^9$, and $R^{10}$ independently can be H or $R^7$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and $R^1$, $R^2$, x and y are as defined herein.

To illustrate, an example of such embodiments can be a polymer having the formula:

wherein $R^1$, $R^2$ and $R^{10}$ independently are a $C_{1-20}$ alkyl group, and n is an integer ranging from 5 to 10,000.

In one aspect, the present teachings relate to molecular semiconducting compounds, as well as the use of these compounds in electronic, optoelectronic, or optical devices. These molecular compounds can be represented by formula (II):

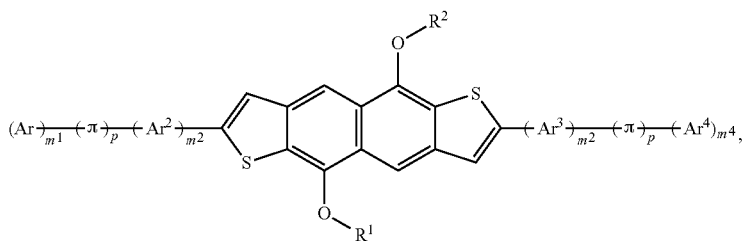

wherein:

R[1] and R[2] independently are a $C_{1-20}$ alkyl group or a $C_{1-20}$ haloalkyl group;

Ar[1], Ar[2], Ar[3], and Ar[4] independently are an optionally substituted $C_{6-14}$ aryl group or an optionally substituted 5-14 membered heteroaryl group;

π, at each occurrence, independently is an optionally substituted polycyclic aryl or heteroaryl group;

$m^1$, $m^2$, $m^3$ and $m^4$ independently are 1, 2, 3 or 4; and p is 0 or 1.

To illustrate, each of R[1] and R[2] independently can be a linear or branched $C_{1-40}$ alkyl groups such as methyl, ethyl, n-propyl, isopropyl, n-butyl, iso-butyl, sec-butyl, tert-butyl, n-pentyl, iso-pentyl, neo-pentyl, n-hexyl, n-dodecyl,

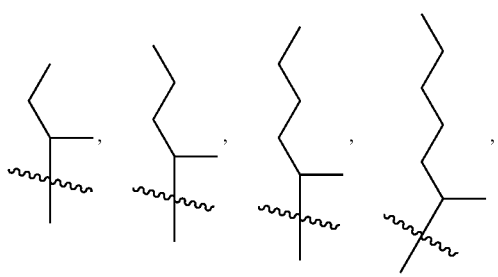

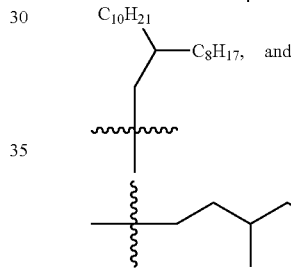

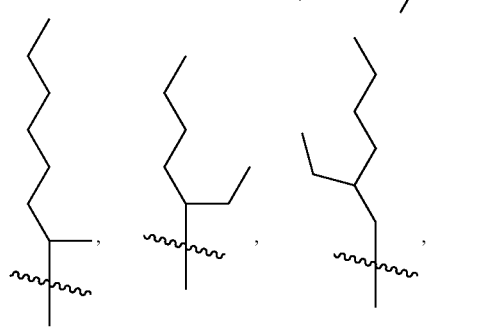

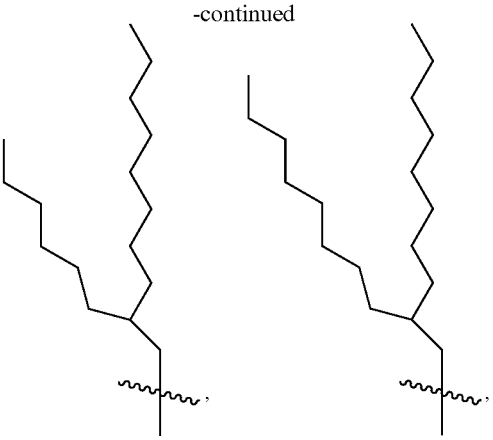

or a linear or branched $C_{1-40}$ haloalkyl groups where one or more hydrogen atoms in, for example, the $C_{1-40}$ alkyl groups shown above, are replaced by a halogen such as F.

Examples of Ar[1], Ar[2], Ar[3], and Ar[4] include various conjugated monocyclic and polycyclic moieties which can be optionally substituted as described herein. For example, each of Ar[1], Ar[2], Ar[3], and Ar[4] optionally can be substituted with 1-6 R[d] groups, where R[d], at each occurrence, independently is selected from a) halogen, b) —CN, c) —NO$_2$, d) —N(R[e])$_2$, e) oxo, f) —OH, g) =C(R[f])$_2$, h) —C(O)R[e], i) —C(O)OR[e], j) —C(O)N(R[e])$_2$, k) —SH, l) —S(O)$_2$—R[e], m) —S(O)$_2$OR[e], n) —(OCH$_2$CH$_2$)$_t$OR[e], o) —CF$_2$CF$_2$)$_t$OR[e], p) —(OCH$_2$CF$_2$)$_t$OR[e], q) —(OCF$_2$CH$_2$)$_t$OR[e], r) —(CH$_2$CH$_2$O)$_t$R[e], s) —(CF$_2$CF$_2$O)$_t$R[e], t) —(CH$_2$CF$_2$O)$_t$R[e], u) —(CF$_2$CH$_2$O)$_t$R[e], v) a $C_{1-40}$ alkyl group, w) a $C_{2-40}$ alkenyl group, x) a $C_{2-40}$ alkynyl group, y) a $C_{1-40}$ alkoxy group, z) a $C_{1-40}$ alkylthio group, aa) a $C_{1-40}$ haloalkyl group, ab) a —Y—$C_{3-10}$ cycloalkyl group, ac) a —Y—$C_{6-14}$ aryl group, ad) a —Y—$C_{6-14}$ haloaryl group, ae) a —Y-3-12 membered cycloheteroalkyl group, and af) a —Y-5-14 membered heteroaryl group, wherein each of the $C_{1-40}$ alkyl group, the $C_{2-40}$ alkenyl group, the $C_{2-40}$ alkynyl group, the $C_{1-40}$ alkoxy group, the $C_{1-40}$ alkylthio group, the $C_{1-40}$ haloalkyl group, the $C_{3-10}$ cycloalkyl group, the $C_{6-14}$ aryl group, the $C_{6-14}$ haloaryl group, the 3-12 membered cycloheteroalkyl group, and the 5-14 membered heteroaryl group is optionally substituted with 1-4 R[f] groups;

R$^c$, at each occurrence, independently is selected from H, a C$_{1-40}$ alkyl group, a C$_{1-40}$ haloalkyl group, and a —Y—C$_{6-14}$ aryl group;

R$^f$, at each occurrence, independently is selected from a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —N(C$_{1-20}$ alkyl)-C$_{6-14}$ aryl, j) —N(C$_{6-14}$ aryl)$_2$, k) —S(O)$_w$H, l) —S(O)$_w$—C$_{1-20}$ alkyl, m) —S(O)$_2$OH, n) —S(O)$_2$—OC$_{1-20}$ alkyl, o) —S(O)$_2$—OC$_{6-14}$ aryl, p) —CHO, q) —C(O)—C$_{1-20}$ alkyl, r) —C(O)—C$_{6-14}$ aryl, s) —C(O)OH, t) —C(O)—OC$_{1-20}$ alkyl, u) —C(O)—OC$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—C$_{6-14}$ aryl, z) —C(O)N(C$_{1-20}$ alkyl)-C$_{6-14}$ aryl, aa) —C(O)N(C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(C$_{6-14}$ aryl)$_2$, af) —C(S)N(C$_{1-20}$ alkyl)-C$_{6-14}$ aryl, ag) —C(S)NH—C$_{6-14}$ aryl, ah) —S(O)$_w$NH$_2$, ai) —S(O)$_w$NH(C$_{1-20}$ alkyl), aj) —S(O)$_w$N(C$_{1-20}$ alkyl)$_2$, ak) —S(O)$_w$NH(C$_{6-14}$ aryl), al) —S(O)$_w$N(C$_{1-20}$ alkyl)-C$_{6-14}$ aryl, am) —S(O)$_w$N(C$_{6-14}$ aryl)$_2$, an) —SiH$_3$, ao) —SiH(C$_{1-20}$ alkyl)$_2$, ap) —SiH$_2$(C$_{1-20}$ alkyl), aq) —Si(C$_{1-20}$ alkyl)$_3$, ar) a C$_{1-20}$ alkyl group, as) a C$_{2-20}$ alkenyl group, at) a C$_{2-20}$ alkynyl group, au) a C$_{1-20}$ alkoxy group, av) a C$_{1-20}$ alkylthio group, aw) a C$_{1-20}$ haloalkyl group, ax) a C$_{3-10}$ cycloalkyl group, ay) a C$_{6-14}$ aryl group, az) a C$_{6-14}$ haloaryl group, ba) a 3-12 membered cycloheteroalkyl group, or bb) a 5-14 membered heteroaryl group;

Y, at each occurrence, independently is selected from a divalent C$_{1-10}$ alkyl group, a divalent C$_{1-10}$ haloalkyl group, and a covalent bond;

t is 1, 2, 3, 4, 5, 6, 7, 8, 9 or 10; and w, at each occurrence, independently is 0, 1, or 2.

Examples of monocyclic (hetero)aryl groups include a phenyl group or a 5- or 6-membered heteroaryl group such as a pyrrolyl group, a furyl group, a thienyl group, a pyridyl group, a pyrimidyl group, a pyridazinyl group, a pyrazinyl group, a triazolyl group, a tetrazolyl group, a pyrazolyl group, an imidazolyl group, an isothiazolyl group, a thiazolyl group, and a thiadiazolyl group. For example, at least one of Ar$^1$, Ar$^2$, Ar$^3$, and Ar$^4$ can include at least one 5-membered heteroaryl group that includes at least one sulfur ring atom. Examples of such sulfur-containing 5-membered heteroaryl group include a thienyl group, a thiazolyl group, an isothiazolyl group, and a thiadiazolyl group, each of which optionally can be substituted with 1-4 R$^3$ groups, where R$^3$, at each occurrence, independently can be selected from a halogen, CN, oxo, =C(CN)$_2$, a C$_{1-40}$ alkyl group, a C$_{1-40}$ haloalkyl group, a C$_{1-40}$ alkoxy group, and a C$_{1-40}$ alkylthio group.

Examples of bicyclic 8-14 membered (hetero)aryl groups include a naphthyl group and various bicyclic (e.g., 5-5 or 5-6) heteroaryl moieties that include at least one sulfur ring atom. Examples of such sulfur-containing bicyclic heteroaryl moieties include a thienothiopheny group (e.g., a thieno[3,2-b]thiopheny group or a thieno[2,3-b]thiophenyl group), a benzothienyl group, a benzothiazolyl group, a benzisothiaz-olyl group, and a benzothiadiazolyl group, each of which optionally can be substituted with 1-4 R$^3$ groups, where R$^3$, at each occurrence, independently can be selected from a halogen, CN, oxo, =C(CN)$_2$, a C$_{1-40}$ alkyl group, a C$_{1-40}$ haloalkyl group, a C$_{1-40}$ alkoxy group, and a C$_{1-40}$ alkylthio group.

By way of example, Ar$^1$, Ar$^2$, Ar$^3$, and Ar$^4$, at each occurrence, independently can be selected from:

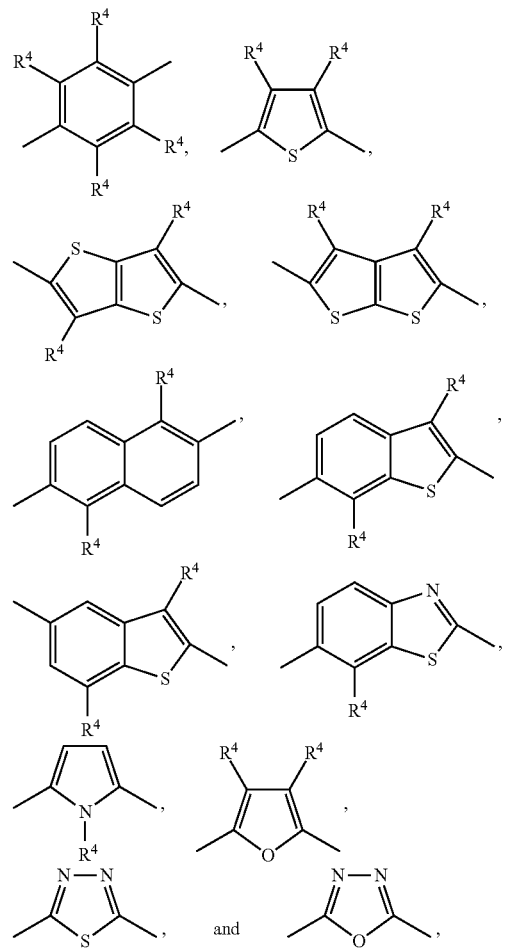

where R$^4$, at each occurrence, independently can be H or R$^3$, and R$^3$ can be selected from a halogen, CN, oxo, =C(CN)$_2$, a C$_{1-40}$ alkyl group, a C$_{1-40}$ haloalkyl group, a C$_{1-40}$ alkoxy group, and a C$_{1-40}$ alkylthio group.

In certain embodiments, Ar$^1$, Ar$^2$, Ar$^3$, and Ar$^4$, at each occurrence, independently can be an optionally substituted thienyl group or an optionally substituted bicyclic heteroaryl group comprising a thienyl group fused with a 5-membered heteroaryl group. In particular embodiments, a molecular semiconducting compound according to the present teachings can have the formula:

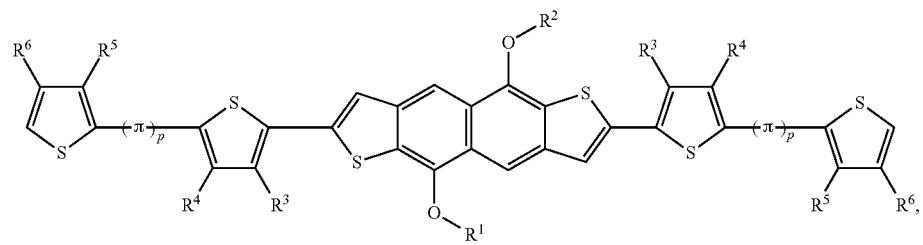

wherein:

$R^3$, $R^4$, $R^5$, and $R^6$, at each occurrence, independently are selected from H and $R^2$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and $R^1$, $R^2$, π, and p are as defined herein.

In certain embodiments, p, at each occurrence, can be 1. In certain embodiments, π can be an optionally substituted heteroaryl group represented by a formula selected from:

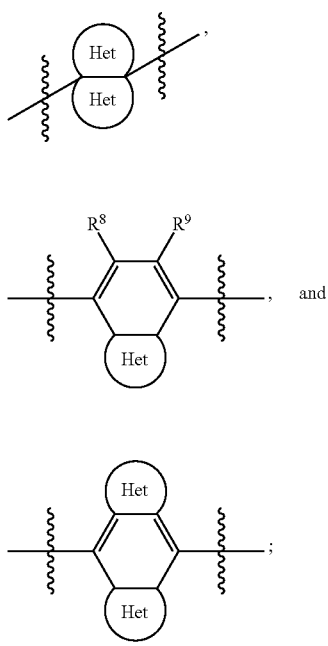

wherein Het, at each occurrence, is a monocyclic moiety including at least one heteroatom in its ring and optionally substituted with 1-2 $R^{10}$ groups, wherein $R^8$, $R^9$, and $R^{10}$ independently can be H or $R^7$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and $R^1$, $R^2$, x and y are as defined herein. In particular embodiments, π can be selected from:

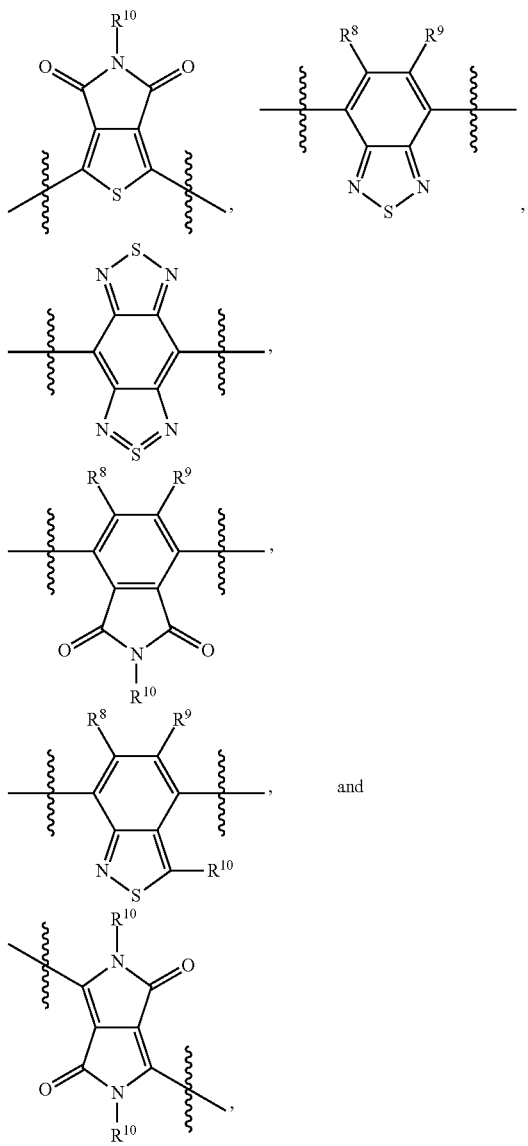

where $R^8$, $R^9$, and $R^{10}$ independently can be selected from H, halogen, CN, a $C_{1-20}$ alkyl group, a $C_{1-20}$ haloalkyl group, a $C_{1-20}$ alkoxy group, and a $C_{1-20}$ alkylthio group.

To illustrate, a molecular semiconducting compound according to the present teachings can have the formula:

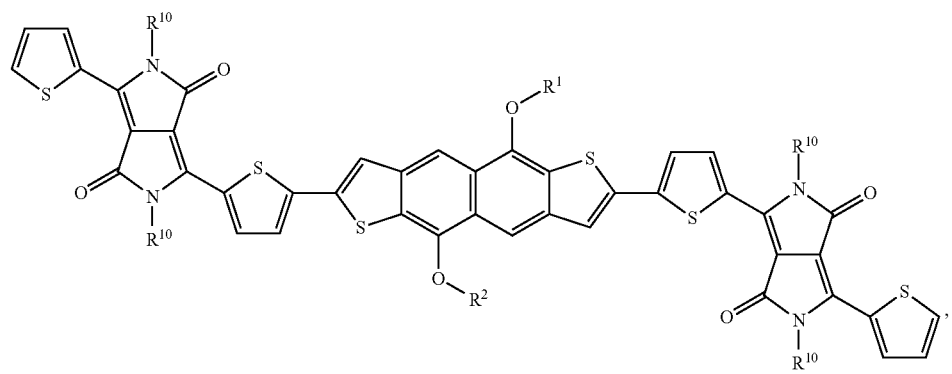

wherein $R^1$, $R^2$ and $R^{10}$ independently can be a $C_{1-20}$ alkyl group.

Compounds of the present teachings can be prepared according to procedures analogous to those described in the Examples. In particular, Stille coupling can be used to prepare polymeric compounds according to the present teachings with high molecular weight and in high yield (≥75%) and purity, as confirmed by $^1$H NMR spectra, elemental analysis, and GPC measurements.

Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatograpy (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Certain embodiments disclosed herein can be stable under ambient conditions ("ambient stable"), soluble in common solvents, and in turn solution-processable into various articles, structures, or devices. As used herein, a compound can be considered "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a polymer according to the present teachings can be described as ambient stable if its carrier mobility or reduction potential does not vary more than 20% or more than 10% from its initial value after exposure to ambient conditions, including, air, humidity and temperature, over a 3 day, 5 day, or 10 day period. Without wishing to be bound by any particular theory, it is believed that the strong electron-depleted electronic structure of the thienocoronene moiety, and in the case of the polymers, the regioregular highly π-conjugated polymeric backbone, can make the present compounds ambient-stable n-channel semiconductor materials without requiring additional π-core functionalization (i.e., core substitution of the thienocoronene moiety) with strong electron-withdrawing functionalities.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

As used herein, "solution-processable" refers to compounds (e.g., thienocoronene-imide copolymers), materials, or compositions that can be used in various solution-phase processes including spin-coating, printing (e.g., inkjet printing, screen printing, pad printing, offset printing, gravure printing, flexographic printing, lithographic printing, mass-printing and the like), spray coating, electrospray coating, drop casting, dip coating, and blade coating.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and micro-contact printing). In other embodiments, the depositing step can be carried out by spin coating, drop-casting, zone casting, dip coating, blade coating, or spraying.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit p-type semiconductor activity, ambipolar activity, light absorption, and/or light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices.

For example, articles of manufacture such as the various devices described herein can be an electronic or optoelectronic device including a first electrode, a second electrode, and a semiconducting component in contact with the first electrode and the electrode, where the semiconducting component includes a compound of the present teachings. These devices can include a composite having a semiconducting component (or semiconductor material) of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., as described in Yoon, M-H. et al., *PNAS*, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown in FIG. 1, an OFET can include a gate dielectric component (e.g., shown as 8, 8', 8", and 8'''), a semiconducting component or semiconductor layer (e.g., shown as 6, 6', 6", and 6'''), a gate electrode or contact (e.g., shown as 10, 10', 10", and 10'''), a substrate (e.g., shown as 12, 12', 12", and 12'''), and source and drain electrodes or contacts (e.g., shown as 2, 2', 2", 2''', 4, 4', 4", and 4'''). As shown, in each of the configurations, the semiconducting component is in contact with the source and drain electrodes and the gate dielectric component.

In certain embodiments, OTFT devices can be fabricated with the present compounds on doped silicon substrates, using $SiO_2$ as the dielectric, in top-contact geometries. In particular embodiments, the active semiconductor layer which incorporates at least a compound of the present teachings can be deposited at room temperature or at an elevated temperature. In other embodiments, the active semiconductor layer which incorporates at least one compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present teachings can be deposited at room temperature or at an elevated temperature. In other embodiments, the active semiconducting layer which incorporates at least a compound of the present teachings can be applied by spin-coating or printing as described herein. Gate and source/drain contacts can be made of Au, other metals, or conducting polymers and deposited by vapor-deposition and/or printing.

In various embodiments, a semiconducting component incorporating compounds of the present teachings can exhibit semiconducting activity, for example, a carrier mobility of $10^{-4}$ cm$^2$/V-sec or greater and/or a current on/off ratio ($I_{on}/I_{off}$) of $10^3$ or greater.

Other articles of manufacture in which compounds of the present teachings are useful are photovoltaics or solar cells. Compounds of the present teachings can exhibit broad optical absorption and/or a tuned redox properties and bulk carrier mobilities, making them desirable for such applications. Accordingly, the compounds described herein can be used as a donor (p-type) semiconductor material in a photovoltaic design, which includes an adjacent n-type semiconductor material that forms a p-n junction. The compounds can be in the form of a thin film semiconductor, which can be deposited on a substrate to form a composite. Exploitation of compounds of the present teachings in such devices is within the knowledge of a skilled artisan.

In various embodiments, a semiconducting component incorporating compounds of the present teachings can enable photovoltaic cells with power conversion efficiency of about 1% or greater.

Figure 2:
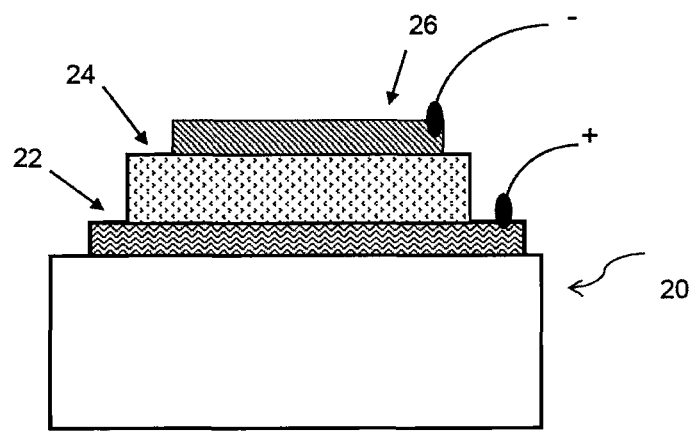
FIG. 2 illustrates a representative structure of a bulk-heterojunction organic photovoltaic device (also known as solar cell), which can incorporate one or more compounds of the present teachings as the donor and/or acceptor materials.
Figure 3:
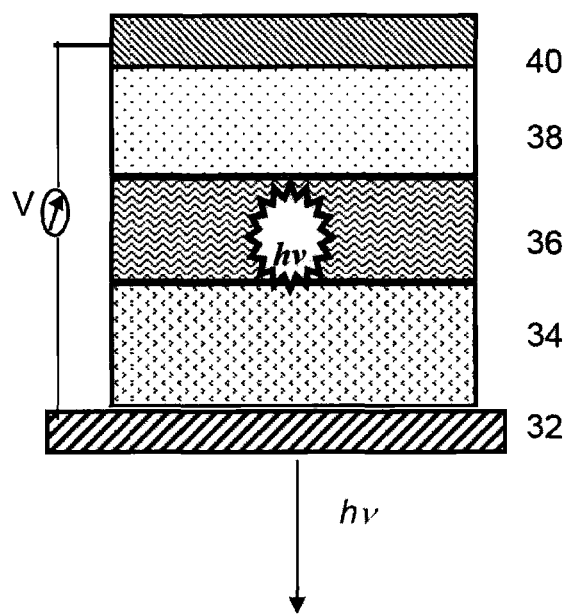
FIG. 3 illustrates a representative structure of an organic light-emitting device, which can incorporate one or more compounds of the present teachings as electron-transporting and/or emissive and/or hole-transporting materials.

Accordingly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) which can incorporate one or more compounds of the present teachings as the donor and/or acceptor materials. As shown, a representative solar cell generally includes a substrate 20 (e.g., glass), an anode 22 (e.g., ITO), a cathode 26 (e.g., aluminium or calcium), and a photoactive layer 24 between the anode and the cathode which can incorporate one or more compounds of the present teachings as the electron donor (p-channel) and/or electron acceptor (n-channel) materials. Optional interlayers (not shown) also can be present. FIG. 3 illustrates a representative structure of an OLED which can incorporate one or more compounds of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more compounds of the present teachings as hole-transporting (n-channel) (layer 34 as shown) and/or emissive (layer 36 as shown) and/or electron-transporting (p-channel) materials (layer 38 as shown). In embodiments where the present compounds only have one or two of the properties of hole transport, electron transport, and emission, the present compounds can be blended with one or more further organic compounds having the remaining required property or properties.

The following examples are provided to illustrate further and to facilitate the understanding of the present teachings and are not in any way intended to limit the invention.

N-Bromosuccinimide (NBS), n-butyllithium (2.5 M in hexanes), BF$_3$.OEt$_2$, Me$_3$SnCl and Pd(PPh$_3$)$_4$ were purchased from Aldrich. Bis(2,2-diethoxyethyl)disulfide was purchased from TCI America. NBS was recrystallized from H$_2$O and all other reagents commercially available were used as received without further purification.

THF was distilled from Na/benzophenone. All reactions were carried out under an inert atmosphere of N$_2$. Analytical thin-layer chromatography (TLC) was performed on aluminum sheets, precoated with silica gel 60-F$_{254}$ (Merck 5554). Flash column chromatography was carried out using silica gel 60 (Silicycle) as the stationary phase. NMR spectra were recorded on either a Bruker Avance III 500 spectrometer or a Varian Unity Plus 500 spectrometer, with working frequencies of 499.4 MHz for $^1$H and 125.6 MHz for $^{13}$C. Chemical shifts are reported in ppm and referenced to the residual non-deuterated solvent frequencies (CDCl$_3$: δ 7.27 ppm for $^1$H, δ 77.0 ppm for $^{13}$C). High resolution mass spectra were recorded on an Agilent 6210 LC-TOF multimode ionization (MMI) mass spectrometer. Electrospray mass spectrometry was performed with a Thermo Finnegan model LCQ Advantage mass spectrometer. UV-Visible spectroscopy was performed on a Varian Cary 5000 UV-Vis-NIR spectrophotometer or a Varian Cary 50 Scan UV-Vis spectrophotometer. Electrochemistry was performed on a C3 Cell Stand electrochemical station equipped with BAS Epsilon software (Bioanalytical Systems, Inc., Lafayette, Ind.). Photoreactions with UV irradiation was carried out in a photochemical reactor Rayonet model RPR 600 MINI (Southern New England Ultraviolet Company) equipped with 254 nm UV ramp. Differential scanning calorimetry (DSC) was performed on TA model DSC 2920 with a heating ramp of 10° C./min and reported for the second heating-cooling cycle. Polymer molecular weights were determined on a Polymer Laboratories PL-GPC 220 using trichlorobenzene as eluent at 150° C. versus polystyrene standards. OFET device measurements were carried out at room temperature in a customized probe station in air. Coaxial and/or triaxial shielding was incorporated into Signatone probes to minimize noise levels. Organic field effect transistor (OFET) characterizations were performed with a Keithley 6430 subfemto ammeter (drain) and a Keithley 2400 (gate) source meter, operated by a locally written Labview program. Thin films were analyzed using wide-angle X-ray diffractometry (WAXRD) on a Rigaku ATX-G using standard θ-2 θ techniques, with monochromatic CuKα radiation. Tapping mode atomic force microscopy (AFM) was performed with a Bruker Dimension ICON. OPV characterization was performed on a Spectra-Nova Class A Solar Simulator with AM1.5G light (100 mW/cm$_2$) from a Xe arc lamp. The light source was calibrated with an NREL-certified Si diode equipped with a KG3 filter to bring spectral mismatch to unity. Current vs potential (J-V) measurements were recorded with a Keithly 2400 digital source meter. External quantum efficiency (EQE) was performed using an Oriel Model S3 QE-PV-SI (Newport Instruments) equipped with an NIST-certified Si-diode and a Merlin lock-in amplifier and optical chopper. Monochromatic light was generated from a 300 W Xe arc lamp.

Example 1

Synthesis of Dialkoxy NDT and BDT Derivatives

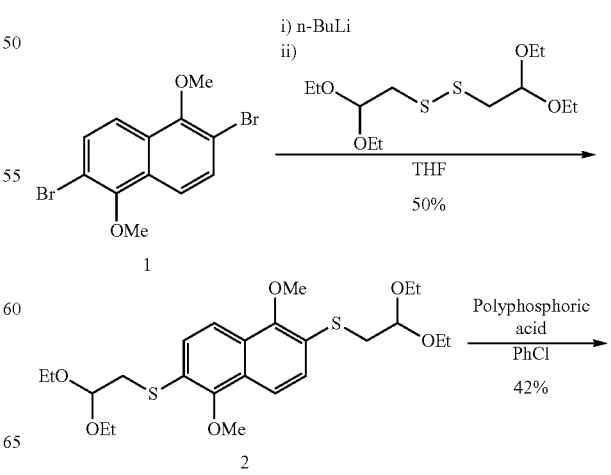

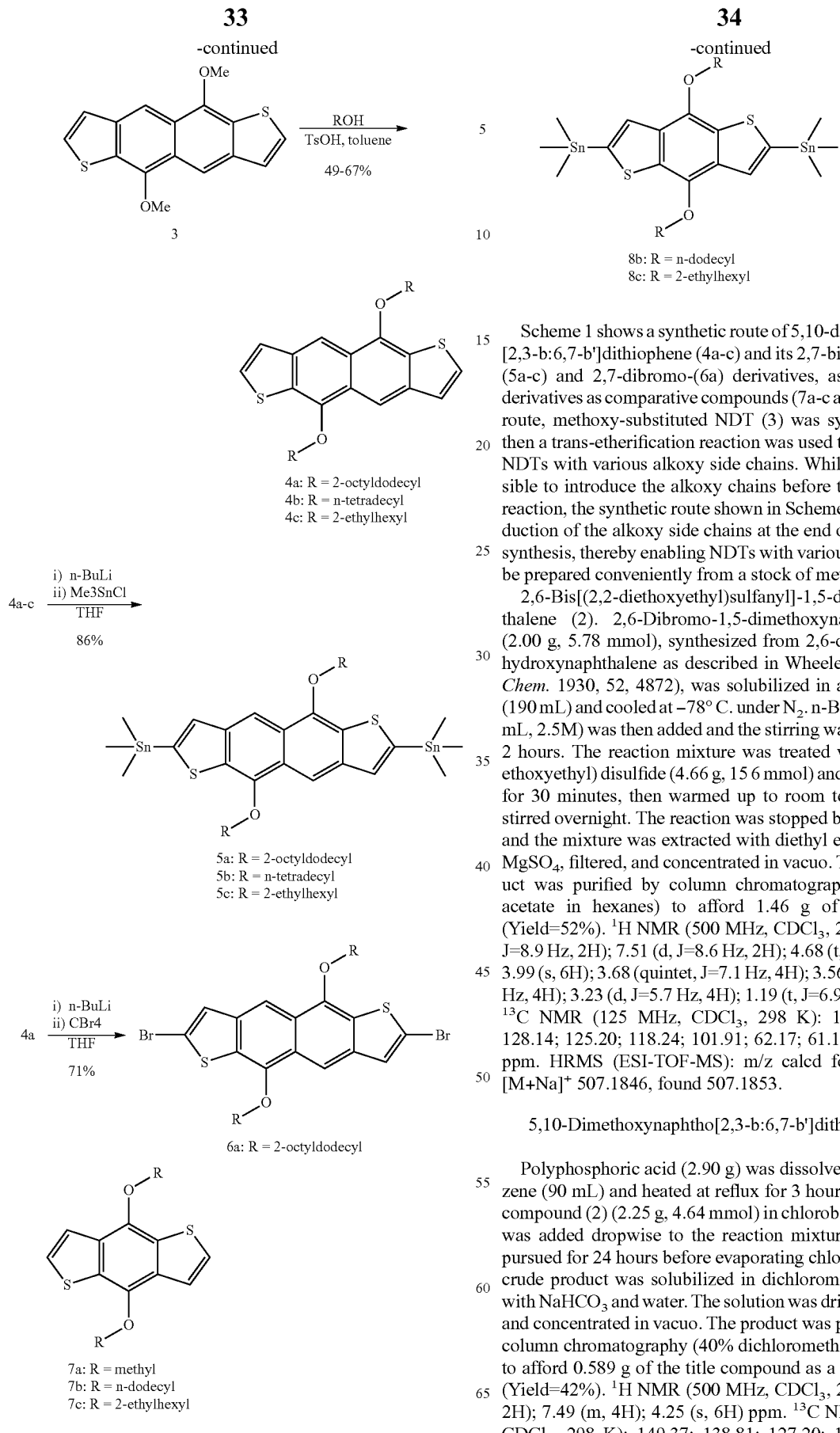

Scheme 1 shows a synthetic route of 5,10-dialkoxynaphtho[2,3-b:6,7-b']dithiophene (4a-c) and its 2,7-bis(trimethyltin)- (5a-c) and 2,7-dibromo-(6a) derivatives, as well as BDT derivatives as comparative compounds (7a-c and 8b-c). In this route, methoxy-substituted NDT (3) was synthesized first, then a trans-etherification reaction was used to convert (3) to NDTs with various alkoxy side chains. While it also is possible to introduce the alkoxy chains before the ring-closure reaction, the synthetic route shown in Scheme 1 allows introduction of the alkoxy side chains at the end of the monomer synthesis, thereby enabling NDTs with various side chains to be prepared conveniently from a stock of methoxy NDT (3).

2,6-Bis[(2,2-diethoxyethyl)sulfanyl]-1,5-dimethoxynaphthalene (2). 2,6-Dibromo-1,5-dimethoxynaphthalene (1) (2.00 g, 5.78 mmol), synthesized from 2,6-dibromo-1,5-dihydroxynaphthalene as described in Wheeler et al., *J. Org. Chem.* 1930, 52, 4872), was solubilized in anhydrous THF (190 mL) and cooled at −78° C. under $N_2$. n-Butyllithium (5.8 mL, 2.5M) was then added and the stirring was continued for 2 hours. The reaction mixture was treated with bis(2,2-diethoxyethyl) disulfide (4.66 g, 15 6 mmol) and kept at −78° C. for 30 minutes, then warmed up to room temperature and stirred overnight. The reaction was stopped by adding water, and the mixture was extracted with diethyl ether, dried over $MgSO_4$, filtered, and concentrated in vacuo. The crude product was purified by column chromatography (30% ethyl acetate in hexanes) to afford 1.46 g of a yellow oil. (Yield=52%). $^1$H NMR (500 MHz, $CDCl_3$, 298 K): 7.80 (d, J=8.9 Hz, 2H); 7.51 (d, J=8.6 Hz, 2H); 4.68 (t, J=5.3 Hz, 2H); 3.99 (s, 6H); 3.68 (quintet, J=7.1 Hz, 4H); 3.56 (quintet, J=7.1 Hz, 4H); 3.23 (d, J=5.7 Hz, 4H); 1.19 (t, J=6.9 Hz, 12H) ppm. $^{13}$C NMR (125 MHz, $CDCl_3$, 298 K): 154.46; 128.40; 128.14; 125.20; 118.24; 101.91; 62.17; 61.11; 36.28; 15.25 ppm. HRMS (ESI-TOF-MS): m/z calcd for $C_{24}H_{36}O_6S_2$ $[M+Na]^+$ 507.1846, found 507.1853.

5,10-Dimethoxynaphtho[2,3-b:6,7-b']dithiophene (3)

Polyphosphoric acid (2.90 g) was dissolved in chlorobenzene (90 mL) and heated at reflux for 3 hours. A solution of compound (2) (2.25 g, 4.64 mmol) in chlorobenzene (17 mL) was added dropwise to the reaction mixture. Stirring was pursued for 24 hours before evaporating chlorobenzene. The crude product was solubilized in dichloromethane, washed with $NaHCO_3$ and water. The solution was dried over $MgSO_4$ and concentrated in vacuo. The product was purified by flash column chromatography (40% dichloromethane in hexanes) to afford 0.589 g of the title compound as a yellow powder. (Yield=42%). $^1$H NMR (500 MHz, $CDCl_3$, 298 K): 8.51 (s, 2H); 7.49 (m, 4H); 4.25 (s, 6H) ppm. $^{13}$C NMR (125 MHz, $CDCl_3$, 298 K): 149.37; 138.81; 127.20; 126.14; 123.61;

123.38; 109.95; 59.64 ppm. HRMS (ESI-TOF-MS): m/z calcd for $C_{16}H_{12}O_2S_2$ 300.0273, found 300.0264.

5,10-Bis(2-octyldodecyloxy)naphtho[2,3-b:6,7-b']dithiophene (4a)

Compound (3) (0.400 g, 1.33 mmol) was weighed into a flame-dried 2-neck flask fitted with a condenser. Toluene (13 mL), 2-octyl-1-dodecanol (1.59 g, 5.32 mmol), and p-toluenesulfonic acid (0.051 g, 0.266 mmol) were then added. The mixture was placed in a 130° C. heat bath and stirred overnight. The mixture was diluted with water, extracted with dichloromethane, dried over MgSO$_4$, filtered and concentrated. The product was purified via column chromatography (10% dichloromethane in hexanes) to yield compound (4a) as a yellow solid (0.735 g, 66%). $^1$H NMR (500 MHz, CDCl$_3$, 298 K): 8.46 (s, 2H); 7.45 (m, 4H); 4.27 (d, J=5.4 Hz, 4H); 2.01 (quintet, J=6.2 Hz, 2H); 1.73 (m, 4H); 1.47 (m, 60H); 0.89 (m, 12H) ppm. $^{13}$C NMR (125 MHz, CDCl$_3$, 298 K): 149.87; 139.70; 127.98; 127.08; 124.83; 124.62; 110.84; 75.85; 39.38; 31.96; 31.42; 30.18; 29.76; 29.71; 29.43; 29.41; 27.06; 22.74; 14.18 ppm. HRMS (ESI-TOF-MS): m/z calcd for $C_{54}H_{88}O_2S_2$ 832.6220, found 832.6217.

5,10-Ditetradecyloxynaphtho[2,3-b:6,7-b']dithiophene (4b)

Compound (3) (0.500 g, 1.66 mmol) was weighed into a flame-dried 2-neck flask fitted with a condenser. Toluene (17 mL), 1-tetradecanol (1.42 g, 6.64 mmol), and p-toluenesulfonic acid (0.063 g, 0.332 mmol) were then added. The mixture was placed in a 130° C. heat bath and stirred overnight. The mixture was diluted with water, extracted with dichloromethane, dried over MgSO$_4$, filtered, and concentrated. The product was purified via column chromatography (20% dichloromethane in hexanes) to yield compound (4b) as a yellow solid (0.540 g, 49%). $^1$H NMR (500 MHz, CDCl$_3$, 298 K): 8.48 (s, 2H); 7.47 (m, 4H); 4.38 (t, J=6.6 Hz, 4H); 2.02 (quintet, J=7.7 Hz, 4H); 1.65 (quintet, J=7.8 Hz, 4H); 1.39 (m, 40H); 0.89 (t, J=7.1 Hz 6H) ppm. $^{13}$C NMR (125 MHz, CDCl$_3$, 298 K): 149.74; 139.68; 128.05; 127.36; 124.87; 124.64; 110.97; 73.54; 31.96; 30.66; 29.73; 29.70; 29.54; 29.40; 26.18; 22.73; 14.17 ppm. HRMS (ESI-TOF-MS): m/z calcd for $C_{42}H_{64}O_2S_2$ 664.4348, found 664.4356.

5,10-Diethylhexyloxynaphtho[2,3-b:6,7-b']dithiophene (4c)

n-Butyllithium (2.5 M solution in hexane, 13.0 mL, 32 5 mmol) was added dropwise to a solution of 2,6-dibromo-1,5-diethylhexyloxynaphthalene (7.04 g, 13 0 mmol) in dry THF (240 ml) at −78° C. The mixture was stirred at this temperature for 2 h and then bis(2,2-diethoxyethyl)disulfide (10.5 g, 35.2 mmol) was added. After stirring for 30 min, the reaction was allowed to warm up to room temperature and stirred overnight. The reaction was quenched with water and extracted with ether (3 Å~100 mL), then dried over MgSO$_4$, filtered, and concentrated in vacuo. Volatile impurities were further removed in vacuo at 150° C. The residue was chromatographed on SiO$_2$ (hexanes-EtOAc, gradient from 99:1 to 97:3) to afford 2,6-bis[(2,2-diethoxyethyl)sulfanyl]-1,5-diethylhexyloxynaphthalene as a yellow oil (6.36 g, 72%). $^1$H NMR (500 MHz, CDCl$_3$, 298 K): ∂=7.77 (d, J=9.0 Hz, 2H), 7.49 (d, J=9.0 Hz, 2H), 4.65 (t, J=5.5 Hz, 2H), 3.96 (d, J=6.0 Hz, 4H), 3.97-3.51 (m, 8H), 3.21 (d, J=5.5 Hz, 4H), 1.94-1.86 (m, 2H), 1.76-1.35 (m, 16H), 1.18 (t, J=7.0 Hz, 12H), 1.03 (t, J=7.0 Hz, 6H), 0.95 (t, J=7.0 Hz, 6H) ppm. $^{13}$C NMR (125 MHz, CDCl$_3$, 298 K): ∂=153.8, 128.7, 128.1, 125.1, 118.0, 102.0, 76.4, 62.1, 40.7, 36.4, 30.3, 29.2, 23.7, 23.1, 15.2, 14.2, 11.3 ppm. Anal. Calcd for $C_{38}H_{64}O_6S_2$: C, 67.02; H, 9.47. Found: C, 67.71; H, 9.39.

A solution of 2,6-bis[(2,2-diethoxyethyl)sulfanyl]-1,5-diethylhexyloxynaphthalene (4.89 g, 7.18 mmol) in dry CH$_2$Cl2 (800 mL) was added dropwise over 4.5 h to a refluxing solution of BF$_3$.OEt$_2$ (2.0 mL, 16 mmol) in dry CH$_2$Cl$_2$ (2000 mL). The mixture was refluxed overnight and poured into sat. NaHCO$_3$ (aq) (1000 mL) and cooled to ambient temperature. The organic layer was separated and combined with CH$_2$Cl$_2$ extracts (2 Å~100 mL), dried over MgSO$_4$, filtered, and concentrated. The residue was chromatographed on SiO$_2$ (hexanes—EtOAc, gradient from 100:0 to 99.3:0.7) to afford the title compound as a yellow powder (495 mg, 14%). $^1$H NMR (500 MHz, CDCl$_3$, 298 K): ∂=8.47 (s, 2H), 7.46 (m, 4H), 4.28 (d, J=5.5 Hz, 4H), 2.00-1.93 (m, 2H), 1.84-1.40 (m, 16H), 1.08 (t, J=7.5 Hz, 6H), 0.95 (t, J=7.5 Hz, 6H) ppm. $^{13}$C NMR (125 MHz, CDCl$_3$, 298 K): ∂=149.8, 139.7, 128.0, 127.1, 124.8, 124.6, 110.8, 75.5, 40.8, 30.5, 29.2, 23.9, 23.2, 14.2, 11.4 ppm. Anal. Calcd for $C_{30}H_{40}O_2S_2$: C, 72.53; H, 8.12. Found: C, 72.68; H, 8.16.

2,7-Bis(trimethylstannyl)-5,10-bis(2-octyldodecyloxy)naphtho[2,3-b:6,7-b']dithiophene (5a)

Compound (4a) (0.350 g, 0.420 mmol) was solubilized in anhydrous THF (17 mL) and cooled at −78° C. under N$_2$. n-Butyllithium (0.42 mL, 2.5M) was then added and the stirring was continued for 30 minutes at this temperature and then 30 minutes at room temperature. The reaction mixture was cooled to −78° C. again before adding trimethylstannyl chloride (1.1 mL, 1.0M). The reaction was warmed up to room temperature and stirred overnight. The reaction was stopped by adding water, and the mixture was extracted with diethyl ether, dried over MgSO$_4$, filtered, and concentrated in vacuo. The crude monomer was solubilized in 5 mL of THF and then dropped in methanol (200 mL). The product was allowed to precipitate in the freezer overnight before filtering and washing with cold methanol to afford a yellow fluffy powder as the title compound (0.420 g, 86%). $^1$H NMR (500 MHz, CDCl$_3$, 298 K): 8.43 (s, 2H); 7.51 (s, 2H); 4.29 (d, J=5.4 Hz, 4H); 2.00 (quintet, J=6.0 Hz, 2H); 1.74 (m, 4H); 1.45 (m, 60H); 0.88 (m, 12H); 0.47 (s, 18H) ppm. $^{13}$C NMR (125 MHz, CDCl$_3$, 298 K): 149.22; 142.73; 141.25; 132.62; 130.19; 124.51; 109.71; 75.50; 39.37; 31.99; 31.97; 31.42; 30.23; 29.83; 29.82; 29.78; 29.75; 29.47; 29.42; 27.08; 22.74; 14.19; 14.18; 8.40 ppm. HRMS (ESI-TOF-MS): m/z calcd for $C_{60}H_{104}O_2S_2Sn_2$ 1158.5516, found 1158.5543.

2,7-Bis(trimethylstannyl)-5,10-ditetradecyloxynaphtho[2,3-b:6,7-b']dithiophene (5b)

Compound (4b) (0.500 g, 0.752 mmol) was solubilized in anhydrous THF (40 mL) and cooled at −78° C. under N$_2$. n-Butyllithium (0.75 mL, 2.5M) was then added and the stirring was continued for 30 minutes at this temperature and then 30 minutes at room temperature. The reaction mixture was cooled to −78° C. again before adding trimethylstannyl chloride (1.9 mL, 1.0M). The reaction was warmed up to room temperature and stirred overnight. The reaction was stopped by adding water, and the mixture was extracted with diethyl ether, dried over MgSO$_4$, filtered, and concentrated in vacuo. The crude monomer was solubilized in 5 mL of THF and then dropped in methanol (200 mL). The product was allowed to precipitate in the freezer overnight before filtering and washing with cold methanol to afford a yellow fluffy powder as the title compound (0.650 g, 86%). $^1$H NMR (500 MHz, CDCl$_3$, 298 K): 8.45 (s, 2H); 7.53 (s, 2H); 4.38 (t, J=6.6 Hz, 4H); 2.01 (quintet, J=7.9 Hz, 4H); 1.65 (quintet, J=7.7 Hz, 4H); 1.39 (m, 40H); 0.89 (t, J=7.0 Hz 6H); 0.47 (s, 18H) ppm. $^{13}$C NMR (125 MHz, CDCl$_3$, 298 K): 149.07; 142.85; 141.22; 132.66; 130.48; 124.58; 109.85; 73.20; 31.96; 30.65; 29.76; 29.73; 29.70; 29.57; 29.41; 26.17; 22.73; 14.17; 8.38 ppm. HRMS (ESI-TOF-MS): m/z calcd for C$_{48}$H$_{80}$O$_2$S$_2$Sn$_2$ 990.3638, found 990.3670.

2,7-Bis(trimethylstannyl)-5,10-bis(2-ethylhexyloxy) naphtho[2,3-b:6,7-b']dithiophene (5c)

n-Butyllithium (2.5 M solution in hexane, 0.6 mL, 1.5 mmol) was added dropwise to a solution of compound (4c) (295.3 mg, 0.595 mmol) in dry THF (50 mL) at −78° C. The mixture was stirred at this temperature for 30 min and then at room temperature for 30 min. After cooling down to −78° C., Me$_3$SnCl (1 M solution in hexane, 1.5 mL, 1.5 mmol) was added dropwise. After stirring for 30 min at this temperature, the reaction was returned to room temperature and stirred overnight. The reaction was quenched with NaHCO$_3$ (aq) and solvent was removed in vacuo. The residue was dissolved in hexane and washed with NaHCO$_3$ aq (1 Å~25 mL) and with water (2 Å~25 mL), then dried over MgSO$_4$, filtered, and concentrated in vacuo. Recrystallization in iPrOH yielded the target compound as a yellow powder (411.2 mg, 84%). $^1$H NMR (500 MHz, CDCl$_3$, 298 K): ∂=8.44 (s, 2H), 7.52 (s, 2H), 4.30 (d, J=5.5 Hz, 4H), 2.00-1.92 (m, 2H), 1.84-1.40 (m, 16H), 1.08 (t, J=7.5 Hz, 6H), 0.98 (t, J=7.0 Hz, 6H), 0.48 (s, 18H) ppm. $^{13}$C NMR (125 MHz, CDCl$_3$, 298 K): ∂=149.2, 142.7, 141.2, 132.6, 130.1, 124.5, 109.6, 75.2, 40.8, 30.5, 29.2, 23.9, 23.2, 14.2, 11.4, -8.4 ppm. Anal. Calcd for C$_{36}$H$_{56}$O$_2$S$_2$Sn$_2$: C, 52.58; H, 6.86. Found: C, 53.03; H, 6.86.

2,7-Dibromo-5,10-bis(2-octyldodecyl)oxynaphtho[2,3-b:6,7-b']dithiophene (6a)

Compound (4a) (0.268 g, 0.322 mmol) was solubilized in anhydrous THF (21 mL) and cooled at −78° C. under N$_2$. n-Butyllithium (0.32 mL, 2.5M) was then added and the stirring was continued for 30 minutes at this temperature and then 30 minutes at room temperature. The reaction mixture was cooled to −78° C. again before adding carbon tetrabromide (0.267 g, 0.805 mmol). The reaction was warmed up to room temperature and stirred overnight. The reaction was stopped by adding water, and the mixture was extracted with diethyl ether, dried over MgSO$_4$, filtered, and concentrated in vacuo. The crude monomer was solubilized in 5 mL of THF and then dropped in methanol (200 mL). The product was allowed to precipitate in the freezer overnight before filtering and washing with cold methanol to afford an orange powder as the title compound (0.226 g, 71%). $^1$H NMR (500 MHz, CDCl$_3$, 298 K): 8.25 (s, 2H); 7.43 (s, 2H); 4.19 (d, J=5.5 Hz, 4H); 1.96 (quintet, J=5.9 Hz, 2H); 1.68 (m, 4H); 1.44 (m, 60H); 0.90 (m, 12H) ppm. $^{13}$C NMR (125 MHz, CDCl$_3$, 298 K): 148.76; 139.25; 128.40; 127.21; 124.71; 117.73; 110.02; 76.00; 39.30; 31.97; 31.33; 30.13; 29.76; 29.75; 29.72; 29.42; 27.01; 22.74; 14.19 ppm. HRMS (ESI-TOF-MS): m/z calcd for C$_{54}$H$_{86}$Br$_2$O$_2$S$_2$ 988.4431, found 988.4418.

Compounds (7a), (7b), (7c), (8b), and (8c) were prepared according to the procedures described in Launay, J.-P. et al., *J. Phys. Chem. B,* 2007, 111, 6788-6797; Hou, J. et al., *Macromolecules,* 2008, 41, 6012-6018; and Liang, Y. et al., *J. Am. Chem. Soc.* 2009, 131, 7792-7799.

Example 2

Characterization of Monomers

Figure 4:
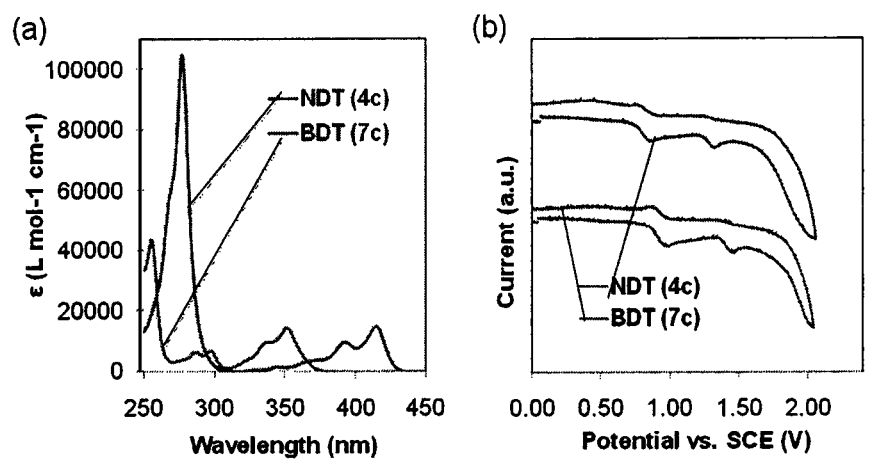
FIG. 4 provides the UV/Vis absorption spectra (a) and cyclic voltammograms (b) of NDT (4c) and BDT (7c).

UV/Vis absorption spectra of NDT with 2-ethylhexyl chains (4c) and analogous BDT (7c) were recorded in dichloromethane solution (5 µM). As shown in FIG. 4, NDT presents a broad and strong absorption up to 430 nm, which is a red-shift of ~60 nm compared to BDT and reasonably confirms its extended π-conjugation. Cyclic voltammograms of 4c and 7c were recorded using a dichloromethane solution in the presence of tetrabutylammonium hexafluorophosphate (Bu$_4$NPF$_6$, 0.1 M) as the electrolyte, and showed their oxidation potentials at 0.34 V and 0.45 V vs. ferrocene/ferrocenium, respectively. This result indicates that HOMO level of NDT is 0.11 eV higher than that of BDT, which is suitable for NDT to work as a more conjugated alternative to BDT to give semiconductor materials with similar or slightly higher HOMO levels.

Example 3

Synthesis of Polymer Semiconductors

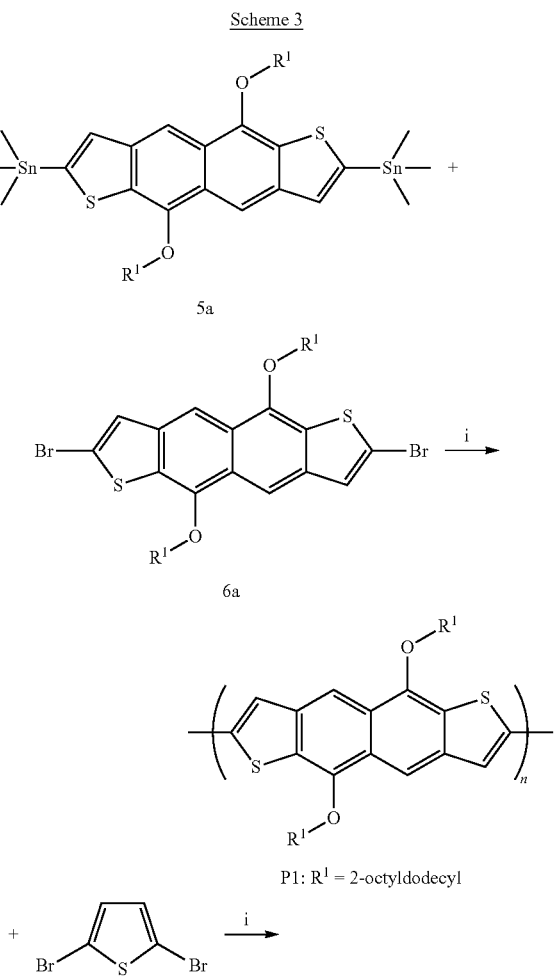

Scheme 3

P1: R$^1$ = 2-octyldodecyl

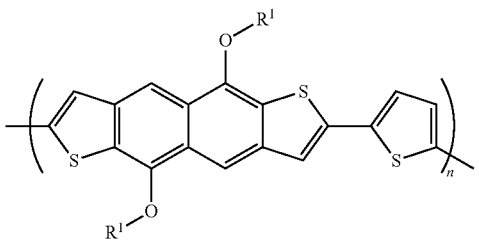

P2: R¹ = 2-octyldodecyl

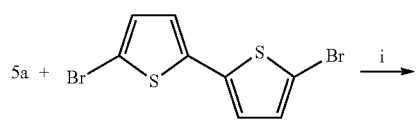

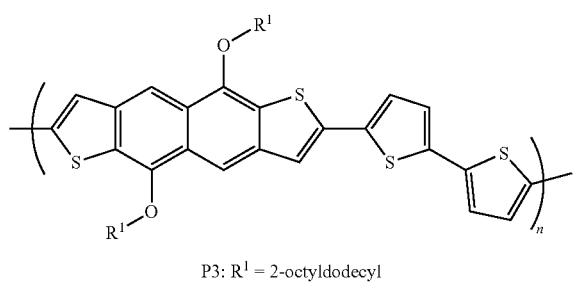

P3: R¹ = 2-octyldodecyl

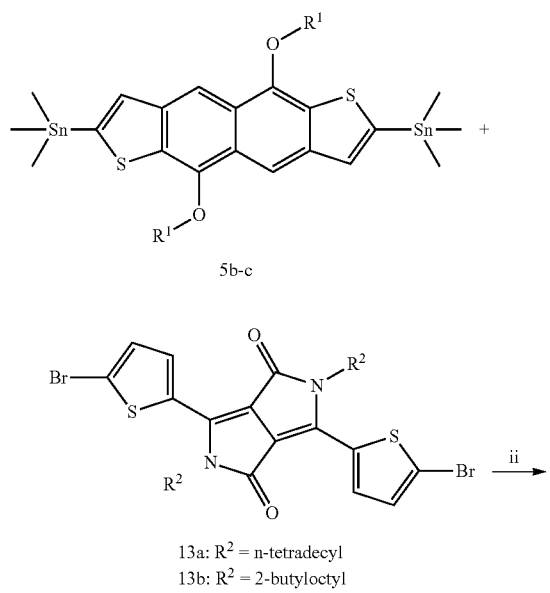

5b-c

13a: R² = n-tetradecyl
13b: R² = 2-butyloctyl

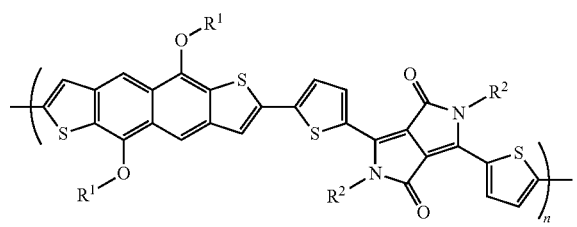

P4a: R¹ = n-tetradecyl, R² = n-tetradecyl
P4b: R¹ = 2-ethylhexyl, R² = 2-butyloctyl

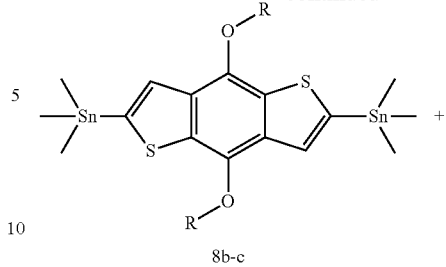

8b-c

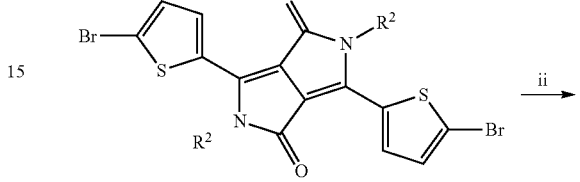

13c: R² = n-dodecyl
13b: R² = 2-butyloctyl

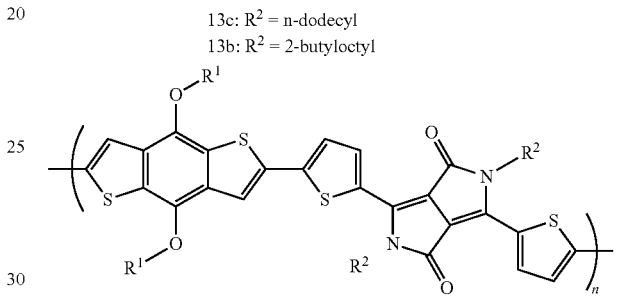

P5a: R¹ = n-dodecyl, R² = n-dodecyl
P5b: R¹ = 2-ethylhexyl, R² = 2-butyloctyl

Scheme 3 shows the synthesis of several different embodiments of the present semiconducting polymers based on NDT: the homopolymer P1, the copolymer with thiophene P2, the copolymer with bithiophene P3, and the copolymer with thiophene-capped diketopyrrolopyrrole (TDPP) P4a-b. Branched and long alkyl chains (2-octyldodecyl) were employed in P1-P3 to ensure the solution processability. For P4a-b, linear alkyl chains (n-tetradecyl) and shorter branched alkyl chains (2-ethylhexyl and 2-butyloctyl) were employed, as the alkyl side chains of comonomer TDPP could help solubility of the resulting copolymers. Copolymers with BDT and TDPP with linear side chains (P5a) and branched side chains (P5b) were also synthesized for comparison to P4a and P4b, respectively. Generally, P1-P5 can be synthesized by Stille coupling reaction using stannylated NDTs (5a-c) or stannylated BDTs (8b-c) and corresponding brominated comonomers shown in Scheme 3. All polymers have good solubility for device fabrication (at least 5 mg/mL) in chloroform or in chlorobenzene.

General Procedure for Synthesis of P1-P3:

The two monomers, $Pd_2dba_3$ (2.8%) and $P(o\text{-}tol)_3$ (11.2%) were loaded in a flame-dried one neck flask mounted with a condenser. Dry and degassed toluene (5 mL) was then added and the reaction was heated to 110° C. under nitrogen for 24 hours. Afterward, end-capping reaction was performed by adding 10% of 2-bromothiophene and 4 hours later 10% of 2-(tributylstannyl)thiophene. After 2 additional hours of stirring the reaction was allowed to cool down to room temperature and dropped into 250 mL of methanol. The resulting solids were subjected to Soxhlet extraction with acetone and hexanes and then dissolved in chloroform. The soluble fraction was concentrated under vacuum, precipitated in methanol, and filtered to give the polymers as dark red solids.

Polymer P1:

This product was obtained as a dark red solid (48% yield). $^1$H NMR (500 MHz, CDCl$_3$, 298 K): 8.35 (br, 2H); 7.71 (br 2H); 4.22 (br, 4H); 1.28 (br, 66H); 0.80 (br, 12H) ppm. $M_n$=13.7 kg/mol, $M_w$=301.6 kg/mol, PDI=22.0.

Polymer P2:

This product was obtained as a dark red solid (95% yield). $^1$H NMR (500 MHz, CDCl$_3$, 298 K): 7.74 (br, 2H); 6.95 (br, 4H); 4.15 (br, 4H); 1.32 (br, 66H); 0.82 (br, 12H) ppm. $M_n$=15.5 kg/mol, $M_w$=48.5 kg/mol, PDI=3.1.

Polymer P3:

This product was obtained as a dark red solid (34% yield). $^1$H NMR (500 MHz, CDCl$_3$, 298 K): 7.07 (br, 4H); 6.70 (br, 4H); 4.06 (br, 4H); 1.29 (br, 66H); 0.84 (m, 12H) ppm. $M_n$=15.7 kg/mol, $M_w$=101.5 kg/mol, PDI=6.5.

Synthesis of Monomers 13a and 13b:

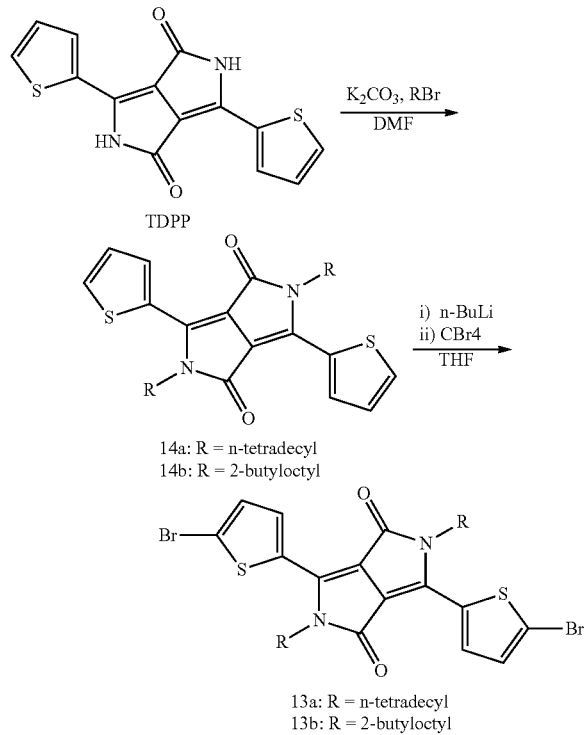

14a: R = n-tetradecyl
14b: R = 2-butyloctyl

13a: R = n-tetradecyl
13b: R = 2-butyloctyl 2,5-Ditetradecyl-3,6-di(thien-2-yl)pyrrolo[3,4-c]pyrrole-1,4-dione (14a)

TDPP (2.20 g, 7.33 mmol) and K$_2$CO$_3$ (4.20 g, 30.4 mmol) were solubilized in anhydrous DMF (50 mL) and heated up to 145° C. under N$_2$. n-tetradecyl bromide (9.40 g, 33.9 mmol) was then added and the stirring was continued overnight at this temperature. The reaction was cooled down to room temperature and poured into iced water (100 g) and extracted with chloroform. The extract was dried over MgSO$_4$, filtered, concentrated in vacuo, and then chromatographed on SiO$_2$ (30% hexanes in chloroform) to afford a dark purple powder as the title compound (2.31 g, 46%). $^1$H NMR (500 MHz, CDCl$_3$, 298 K): 8.94 (m, 2H); 7.65 (m, 2H); 7.30 (m, 2H); 4.08 (t, J=7.9 Hz, 4H); 1.75 (quintet, J=7.8 Hz, 4H); 1.42 (quintet, J=7.5 Hz, 4H); 1.26 (m, 40H); 0.88 (t, J=7.1 Hz, 6H) ppm. $^{13}$C NMR (125 MHz, CDCl$_3$, 298 K): 161.36; 140.01; 135.26; 130.69; 129.75; 128.60; 107.74; 42.21; 32.79; 31.91; 29.94; 29.64; 29.56; 29.52; 29.42; 29.35; 29.24; 26.86; 25.71; 22.69; 14.13 ppm. HRMS (ESI-TOF-MS): m/z calcd for C$_{42}$H$_{64}$N$_2$O$_2$S$_2$ [M+H]$^+$ 693.4482, found 693.4473.

2,5-Bis(2-butyloctyl)-3,6-di(thien-2-yl)pyrrolo[3,4-c]pyrrole-1,4-dione (14b)

TDPP (2.20 g, 7.33 mmol) and K$_2$CO$_3$ (4.21 g, 30.5 mmol) was solubilized in anhydrous DMF (50 mL) and heated up to 145° C. under N$_2$. 2-Butyloctyl bromide (8.55 g, 34.3 mmol) was then added and the stirring was continued overnight at this temperature. The reaction was cooled down to room temperature and poured into iced water (100 g) and filtered with suction. The solid was dissolved in chloroform and concentrated in vacuo, and then chromatographed on SiO$_2$ (40% hexanes in chloroform) to afford a dark purple powder as the title compound (1.08 g, 23%). $^1$H NMR (500 MHz, CDCl$_3$, 298 K): 8.87 (m, 2H); 7.64 (m, 2H); 7.28 (m, 2H); 4.03 (d, J=7.8 Hz, 4H); 1.91 (quintet, J=5.5 Hz, 2H); 1.30-1.21 (m, 32H); 0.84 (m, 12H) ppm. $^{13}$C NMR (125 MHz, CDCl$_3$, 298 K): 161.75; 140.42; 135.19; 130.50; 129.80; 128.39; 107.90; 46.15; 37.68; 31.74; 31.11; 30.84; 29.66; 28.37; 26.14; 23.05; 22.62; 14.08; 14.03 ppm. HRMS (ESI-TOF-MS): m/z calcd for C$_{38}$H$_{56}$N$_2$O$_2$S$_2$ [M+H]$^+$ 637.3856, found 637.3857.

3,6-Bis(5-bromo-2-thienyl)-2,5-ditetradecylpyrrolo[3,4-c]pyrrole-1,4-dione (13a)

Protected from light, NBS (870 mg, 4.89 mmol) was added in portions to a solution of 14a (1.54 g, 2.22 mmol) in chloroform (60 mL) at room temperature. The reaction was stirred at room temperature overnight and poured into 100 mL of methanol, and filtered with suction. The residue was chromatographed on SiO$_2$ (30% hexanes in chloroform) to afford a dark purple solid as the title compound (480 mg, 25%). $^1$H NMR (500 MHz, CDCl$_3$, 298 K): 8.70 (d, J=4.2 Hz, 2H); 7.25 (d, J=4.2 Hz, 2H); 3.99 (t, J=7.8 Hz, 4H); 1.72 (quintet, J=7.5 Hz, 4H); 1.41 (m, 4H); 1.28 (m, 40H); 0.88 (t, J=7.0 Hz, 6H) ppm. $^{13}$C NMR (125 MHz, CDCl$_3$, 298 K): 161.03; 138.99; 135.37; 131.63; 131.07; 119.16; 107.75; 42.27; 31.91; 29.96; 29.68; 29.64; 29.55; 29.47; 29.35; 29.18; 26.80; 22.69; 14.13 ppm. HRMS (ESI-TOF-MS): m/z calcd for C$_{42}$H$_{62}$Br$_2$N$_2$O$_2$S$_2$ 848.2614, found 848.2572.

3,6-Bis(5-bromo-2-thienyl)-2,5-bis(2-butyloctyl)pyrrolo[3,4-c]pyrrole-1,4-dione (13b)

Protected from light, NBS (268 mg, 1.51 mmol) was added in portions to a solution of 14b (436 mg, 0.684 mmol) in chloroform (20 mL) at room temperature. The reaction was stirred at room temperature overnight and poured into 25 mL of methanol, and filtered with suction. The residue was chromatographed on SiO$_2$ (40% hexanes in chloroform) to afford a dark purple solid as the title compound (332 mg, 61%). $^1$H NMR (500 MHz, CDCl$_3$, 298 K): 8.63 (d, J=4.2 Hz, 2H); 7.23 (d, J=4.2 Hz, 2H); 3.93 (d, J=7.8 Hz, 4H); 1.89 (quintet, J=5.5 Hz, 2H); 1.30-1.21 (m, 32H); 0.85 (m, 12H) ppm. $^{13}$C NMR (125 MHz, CDCl$_3$, 298 K): 161.41; 139.40; 135.30; 131.43; 131.11; 118.97; 107.99; 46.28; 37.70; 31.75; 31.07; 30.79; 29.64; 28.33; 26.10; 23.02; 22.62; 14.09; 14.02 ppm. HRMS (ESI-TOF-MS): m/z calcd for C$_{38}$H$_{54}$Br$_2$N$_2$O$_2$S$_2$ [M+H]$^+$ 793.2066, found 793.2040.

3,6-Bis(5-bromo-2-thienyl)-2,5-bis(n-dodecyl)pyrrolo[3,4-c]pyrrole-1,4-dione (13c) and TDPP were synthesized according to the procedures described in Tamayo, A. B. et al., *J. Physc. Chem. C*, 2008, 112, 15543-15552.

General Procedure for Synthesis of P4-P5:

The two monomers and Pd(PPh$_3$)$_4$ (10 mol %) in anhydrous toluene (5 mL) were heated at 110° C. with stirring under nitrogen for three days. Afterward, end-capping reaction was performed by adding 10% of 2-bromothiophene and 4 hours later 10% of 2-(tributylstannyl)thiophene. After 2 additional hours of stirring the reaction was allowed to cool down to room temperature and dropped into methanol. The resulting solids were subjected to Soxhlet extraction with acetone and hexanes, then dissolved in chloroform and chlorobenzene by Soxhlet extraction, precipitated in methanol, and filtered to give the copolymer as a purple solid.

Polymer P4a:

This product was obtained as a dark purple solid (73% yield). $^1$H NMR (500 MHz, C$_2$D$_2$Cl$_4$, 403 K): 8.92 (br, 2H); 8.48 (br, 2H); 7.59 (br, 4H); 4.54 (br, 4H); 4.22 (br, 4H); 2.13-0.96 (m, 108H) ppm. M$_n$=1.1 kg/mol, M$_w$=20.2 kg/mol, PDI=17.6. (Low M$_n$ and high PDI may probably due to aggregation in trichlorobenzene solution even at high temperature of 150° C.)

Polymer P4b:

This product was obtained as a dark purple solid (60% yield). $^1$H NMR (500 MHz, CDCl$_3$, 298 K): 9.10 (br, 2H); 8.04 (br, 2H); 7.06 (br, 4H); 4.27 (br, 8H); 1.78-0.78 (m, 76H) ppm. M$_n$=13.6 kg/mol, M$_w$=79.6 kg/mol, PDI=5.8.

Polymer P5a:

This product was obtained as a dark purple solid (35% yield). $^1$H NMR (500 MHz, C$_2$D$_2$Cl$_4$, 403 K): 8.90 (br, 2H); 7.74 (br, 2H); 7.54 (br, 2H); 4.46 (br, 4H); 4.19 (br, 4H); 2.04-0.96 (m, 92H) ppm. M$_n$=2.7 kg/mol, M$_w$=35.7 kg/mol, PDI=13.3. (Low M$_n$ and high PDI may probably due to aggregation in trichlorobenzene solution even at high temperature of 150° C.)

Polymer P5b:

This product was obtained as a dark purple solid (89% yield). $^1$H NMR (500 MHz, CDCl$_3$, 298 K): 9.21 (br, 2H); 7.64 (br, 2H); 7.14 (br, 2H); 4.15 (br, 8H); 1.85-0.80 (m, 76H) ppm. M$_n$=12.9 kg/mol, M$_w$=114.4 kg/mol, PDI=8.8.

Example 4

Characterization of Polymer Semiconductors

Figure 5:
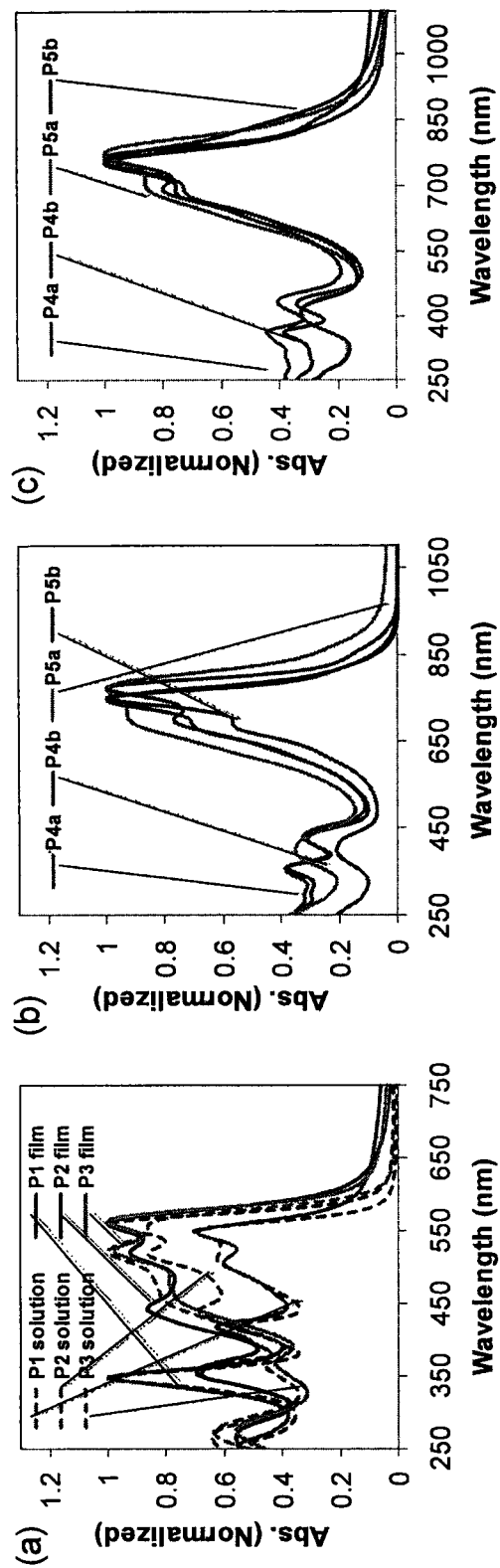
FIG. 5 shows optical absorption spectra of polymer P1-P3 solutions in chloroform and films (a), P4-P5 solutions (b), and P4-P5 films (c). Polymer films were deposited on quartz substrate by spin coating from chloroform solution (5 mg/mL).

UV/Vis absorption spectra of these polymers were collected in solution and as thin films, and depicted in FIG. 5. The homopolymer P1 shows an absorption peak at 347 nm and relatively weaker absorption around 430-550 nm both in solution and as thin film. As the number of thiophene increases from 0 (P1), 1 (P2) to 2 (P3) in the repeating unit, the absorption at low energy region (450-570 nm) is greatly enhanced with vibronic structure while the absorption peak of P1 at 347 nm gets relatively weaker with a slight red shift to 367 nm. These observations can be understood as a result of greater π-conjugation with enhanced order which is also seen in regioregular polythiophenes. For P1-P3, absorption spectra of thin films are almost identical to those in solutions except for the larger peak at 441 nm in P2. Copolymer with TDPP (P4 and P5) have broad absorption up to >900 nm with absorption maxima around 760 nm due to their low band gap energy induced by the copolymerization of electron-donating monomer (NDT and BDT) and electron-deficient monomer (TDPP). In solution, polymers with branched alkyl chains P4b and P5b have very similar absorption profiles, from the peak at 750 nm to the low energy end (~865 nm). In contrast, polymers with linear alkyl chains P4a and P5a show broader absorption than P4b and P5b, respectively, to varying degrees. This suggests that polymers with linear alkyl chains aggregate to form strong π-π interactions in solution, whereas those with branched chains do not. These observations have good agreement with the relatively poor solubility of the polymers with linear chains. Thin film absorption spectra of P4a, P4b and P5b exhibit a shoulder at longer wavelength (around 840-900 nm) compared to those in solution, while P5a have almost identical spectra in this region between solution and thin film. This shoulder indicates greater organization in solid state for P4a, P4b and P5b compared to the solution phase and, on the other hand, P5a has similar degree of organization in solution and in solid state due to the aggregation in solution as discussed above. Note that the absorption shoulders of P5a and P5b are larger than those of P4a and P4b, indicating that BDT-based polymers have greater solid state ordering than NDT-based polymers. The optical band gaps ($E_g^{opt}$) of the polymers are estimated from the red absorption edge and shown in Table 1. P1-P3 have band gaps in the range of 2.00-2.08 eV which are similar to the band gaps of BDT-based polymers previously reported in Hou, J. et al., *Macromolecules*, 2008, 41, 6012-6018. As described above, P4 and P5 have a low band gap ranging from 1.33 to 1.38 eV due to the electron-deficient feature of TDPP unit.

TABLE 1

Optical and Electrochemical Properties of P1-P5

| | $E_g^{opt}$ (eV)[a] | $E_{ox}^{onset}$ (eV)[b] | HOMO (eV)[c] | LUMO (eV)[d] |
|---|---|---|---|---|
| P1 | 2.08 | 0.54 | −5.34 | −3.26 |
| P2 | 2.00 | 0.39 | −5.19 | −3.19 |
| P3 | 2.04 | 0.46 | −5.26 | −3.22 |
| P4a | 1.35 | 0.40 | −5.20 | −3.85 |
| P4b | 1.38 | 0.37 | −5.17 | −3.79 |
| P5a | 1.36 | 0.39 | −5.19 | −3.83 |
| P5b | 1.33 | 0.48 | −5.28 | −3.95 |

[a]Optical band gap estimated from absorption edge of polymer films.
[b]Electrochemically determined vs Fc/Fc$^+$.
[c]HOMO = −($E_{ox}^{onset}$ + 4.80).
[d]LUMO = HOMO + $E_g^{opt}$.

Example 5

Transistor Device Fabrication and Characterization

The charge transport properties of the present polymers were studied using bottom-gate top-contact OFET devices. The OFET devices were fabricated on either hexamethyldisilazane (HMDS)-treated or octadecyltrichlorosilane (OTS)-treated p-doped Si (100) wafers with 300 nm of thermally grown SiO$_2$ as dielectric layer. The capacitance of the 300 nm SiO$_2$ gate insulator is ~12 nF·cm$^{-2}$. Si wafers were cleaned by sonication in ethanol followed by 5 minutes of O$_2$ plasma. Trimethylsilation of the Si/SiO$_2$ surface was completed by exposure of the Si wafer to HMDS vapor in an air-free reaction vessel under N$_2$ at room temperature. OTS-treatment of the Si/SiO$_2$ surface was completed by exposure of the Si wafer to a ethanol solution of OTS in an air-free reaction vessel under N$_2$ at room temperature. Polymer films were deposited by spin-coating from 5 mg/mL or 10 mg/mL chloroform or chlorobenzene solutions in air. After spin-coating the semiconductor films of P1-P5, the films were annealed under vacuum at selected temperatures, as summarized in Table 2. To complete the device fabrication, 50 nm of Au was thermally evaporated through a shadow mask at ~1×10$^{-6}$ Torr to yield the source and drain electrodes with a channel length and width of 100 and 5000 μm, respectively. Device characterization was carried out either under vacuum or in air.

To allow comparison with other organic FETs, mobilities (μ) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current, $V_{DS}$ is the potential between the source and drain, and $V_G$ is the gate voltage). At large $V_{DS}$, the current saturates and is given by:

$$(I_{DS})_{sat} = (WC_i/2L)\mu(V_G - V_t)^2 \quad (1)$$

where L and W are the device channel length and width, respectively, $C_i$ is the capacitance of the oxide insulator (~10 nF/cm² for ~300 nm $SiO_2$), and $V_t$ is the threshold voltage. Mobilities (μ) were calculated in the saturation regime by rearranging equation (2):

$$\mu_{sat} = (2I_{DS}L)/[WC_i(V_G - V_t)^2] \quad (2)$$

The threshold voltage ($V_t$) can be estimated as the X-axis intercept of the linear section of the plot of $V_G$ versus $I_{DS}^{1/2}$ (at $V_{DS} = -100$ V).

TABLE 2

OFET Device Performances for P1-P5
Measured in Ambient Conditions

| | Substrate treatment | $T_{annealing}$ (° C.) | $\mu_h$ (cm² V⁻¹ s⁻¹) | $V_T$ (V) | $I_{on}/I_{off}$ |
|---|---|---|---|---|---|
| P1[a] | HMDS | 150 | NA | NA | NA |
| P2[a] | HMDS | 150 | 2 × 10⁻⁵ | −10 | 10⁴ |
| P3[a] | HMDS | 150 | 7 × 10⁻⁵ | −14 | 10³ |
| P4a | OTS | 240 | 0.1 | −2 | 10⁴ |
| P4b | OTS | 200 | 0.04 | 0.1 | 10⁴ |
| P5a | OTS | 240 | 0.06 | 4 | 10³ |
| P5b | OTS | 240 | 4 × 10⁻³ | 1 | 10⁴ |

[a]Measured under vacuum.

Figure 6:
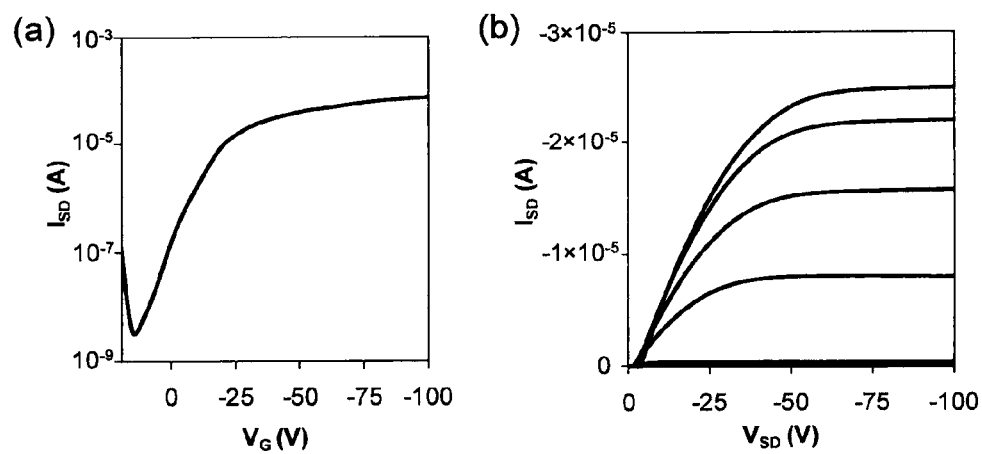
FIG. 6 provides OFET response plots for polymer P4a-based device: (a) transfer plot at $V_{SD}=-100$ V; and (b) output plot at $V_G$ ranging from 0 V to $-100$ V.

As shown in Table 3, the copolymers based on NDT and TDPP (P4a-b) exhibited a p-type transistor operation with a high hole mobility up to 0.1 cm²·V⁻¹·s¹ and on/off ratio of 10⁴ with an optimized device fabrication condition, whereas P2 and P3 exhibited a moderate hole mobility of 2×10⁻⁵ cm²·V⁻¹·s⁻¹ and 7×10⁻⁵ cm²·V⁻¹·s⁻¹, respectively, and P1 did not show any transistor activity. Representative transfer and output plots of P4a-based OFET devices are shown in FIG. 6. As the optimized conditions for OFET device fabrication of P4a-b, polymer films were deposited on OTS-treated substrate (contact angle ~103°) and annealed at relatively high temperature of 200° C. or 240° C. OTS is selected as many high performance polymers based on TDPP have been reported devices on OTS and higher mobility was observed with P4b on OTS than on HMDS. The effect of alkoxy side chains on OFET performances was studied, and linear chains (P4a) were found to give higher performances ($\mu_h$=0.1 cm²·V⁻¹·s⁻¹) than branched chains (P4b: $\mu_h$=0.04 cm²·V⁻¹·s⁻¹) Without wishing to be bound to any to any particular theory, the higher performance with linear chains over branched chains can be understood as a result of better organization and π-π stacking in thin films as shown in UV/Vis spectra. For a comparison between NDT and BDT, OFET devices with BDT-based polymers (P5a-b) were fabricated and tested. The hole mobilities are 0.06 cm⁻²·V⁻¹·s⁻¹ with P5a and 4×10⁻³ cm²·V⁻¹·s⁻¹ with P5b, both lower than those of the corresponding NDT-based polymers P4a ($\mu_h$=0.1 cm²·V⁻¹·s⁻¹) and P4b ($\mu_h$=0.04 cm²·V⁻¹·s⁻¹). Interestingly, as shown in the previous section, UV/Vis spectra of NDT-based polymers have less pronounced shoulders near the red absorption edge compared to BDT-based polymers, which indicates smaller degree of solid state ordering and thus is unfavorable for effective intermolecular charge transport. Without wishing to be bound to any particular theory, it was speculated that other factors such as intrinsic properties of the monomers, or microstructural and morphological characteristics of the polymer films in relation to the actual device architecture, could be affecting the device performances. Note that extended π-conjugation of NDT to promote intermolecular orbital overlap and/or the low reorganization energy in NDT core discussed above could possibly be contributing the high mobility in NDT-based polymers.

X-ray diffraction (XRD) and atomic force microscopy (AFM) analyses were conducted to evaluate the microstructures and morphologies of the polymer films. XRD of P1 indicated low crystallinity compared to the other polymers and no significant grains were observed in the AFM image. This amorphous-like feature of P1 is unfavorable for effective intermolecular charge transport and should be one of the reasons for no activity in OFET devices. The lack of order observed is probably due to the high density of bulky octyl-dodecyl side chains within the homopolymer. On the other hand, AFM images of P2 and P3 show noticeable grains, which should favor intermolecular charge transport. However, the diffraction pattern in P2 film is almost featureless. By comparison, the better performing polymers P4 and P5 show more pronounced grains in AFM images and larger diffraction peaks are observed compared to P2 and P3. These results show a good correlation between high degree of solid-state ordering and high performances in OFET devices. For the copolymers with TDPP (P4a-b and P5a-b), XRD confirmed the clear trend that linear chains promote crystallinity and would reasonably explain the OFET performances of these polymers. The diffraction patterns of P4a and P5a (with linear chains) show distinct peaks up to third order, which indicates highly crystalline order in the polymer films, whereas only a single peak is observed for P4b and P5b (with branched chains). Likewise, AFM images of polymers with linear chains present crystalline grains with larger size than those of polymers with branched chains. These results are also in good agreement with the red-shift in UV/Vis absorption spectra with linear chains compared to those with branched chains. As for comparison between BDT and NDT cores, BDT-based polymer P5a and P5b showed a similar diffraction pattern to the NDT-based P4a and P4b, respectively, although slight differences in the peak shape could be noticed between P4b and P5b. On the other hand, AFM images show significant differences in morphology between BDT-based and NDT-based polymers. BDT-based P5b presents a fibril-like feature, which can be found in previously reported high-performance polymers, whereas NDT-based P4b presents random-shaped grains. Without wishing to be bound to any particular theory, it was speculated that the fibrils of P5b do not have sufficient contacts between each other in terms of orbital overlap and thus inter-fibril charge carrier transport is not efficient. The slight difference in the peak shape of XRD between P4b and P5b could be understood as a result of this morphology difference. The best performing NDT-based polymer with linear side chains, P4a, presents similar grain shapes in its AFM image to P4b (with branched chains) but much larger grain size. As discussed above, the large grain size and high crystallinity should contribute the high mobility with this polymer ($\mu_h$=0.1 cm$^2$·V$^{-1}$·s$^{-1}$). The analogous BDT-based polymer P5a shows even larger grain size than P4a, but the mobility ($\mu_h$=0.06 cm$^2$·V$^{-1}$·s$^{-1}$) is not as high as that of P4a. There are noticeable gaps between grains in its AFM image and these grain boundaries could possibly be limiting the performance of this polymer. Note that it is difficult to quantify grain boundaries from AFM images and NDT-based polymers P4a and P4b might have similar degree of grain boundaries as P5a and P5b. However, P4a exhibits a high mobility of 0.1 cm$^2$·V$^{-1}$·s$^{-1}$, and even P4b with rather low crystallinity and small grain size also exhibits a relatively high mobility of 0.04 cm$^2$·V$^{-1}$·s$^{-1}$. Without wishing to be bound to any particular theory, it is proposed that the extended π-conjugation of NDT core provides a good chance of intermolecular orbital overlap even in less crystalline region such as grain boundaries.

Example 6

Synthesis and Characterization of NDT(TDPP)$_2$ 12H) ppm. $^{13}$C NMR (125 MHz, CDCl$_3$, 298 K): ∂=161.6, 161.5, 140.9, 138.9, 135.6, 135.1, 131.4, 131.2, 130.9, 129.7, 128.5, 118.6, 108.1, 107.7, 45.9, 45.9, 39.1, 39.0, 30.1, 30.1, 28.3, 23.5, 23.5, 23.0, 23.0, 14.0, 10.4 ppm. HRMS (ESI-TOF-MS): m/z calcd for C$_{30}$H$_{40}$BrN$_2$O$_2$S$_2$ [M+H]+ 603.1714. found 603.1715. Anal. Calcd for C$_{30}$H$_{39}$BrN$_2$O$_2$S$_2$: C, 59.69; H, 6.51. Found: C, 59.72; H, 6.45.

NDT(TDPP)$_2$:

Dry toluene (10 mL) and dry DMF (2 mL) were added to compound 5c (80.4 mg, 0.0978 mmol), TDPP-Br (147 mg, 0.243 mmol) and Pd(PPh$_3$)$_4$ (11.5 mg, 0.00996 mmol). The reaction was heated to 120° C. and stirred for 24 h, then poured into MeOH (150 mL) and stirred for 20 min. The resulting precipitate was collected by vacuum filtration and chromatographed on SiO$_2$ (hexanes—CHCl$_3$, gradient from 30:70 to 0:100) to afford the title compound as a shiny, bronze-colored solid (120 mg, 80%). $^1$H NMR (500 MHz, CDCl$_3$, 298 K): ∂=8.97 (d, J=4.5 Hz, 2H), 8.95 (d, J=4.0 Hz, 2H), 8.35 (s, 2H), 7.65-7.64 (m, 4H), 7.50 (d, J=4.0 Hz, 2H), 7.29 (d, J=4.5 Hz, 2H), 4.30 (d, J=5.5 Hz, 4H), 4.14-4.02 (m,

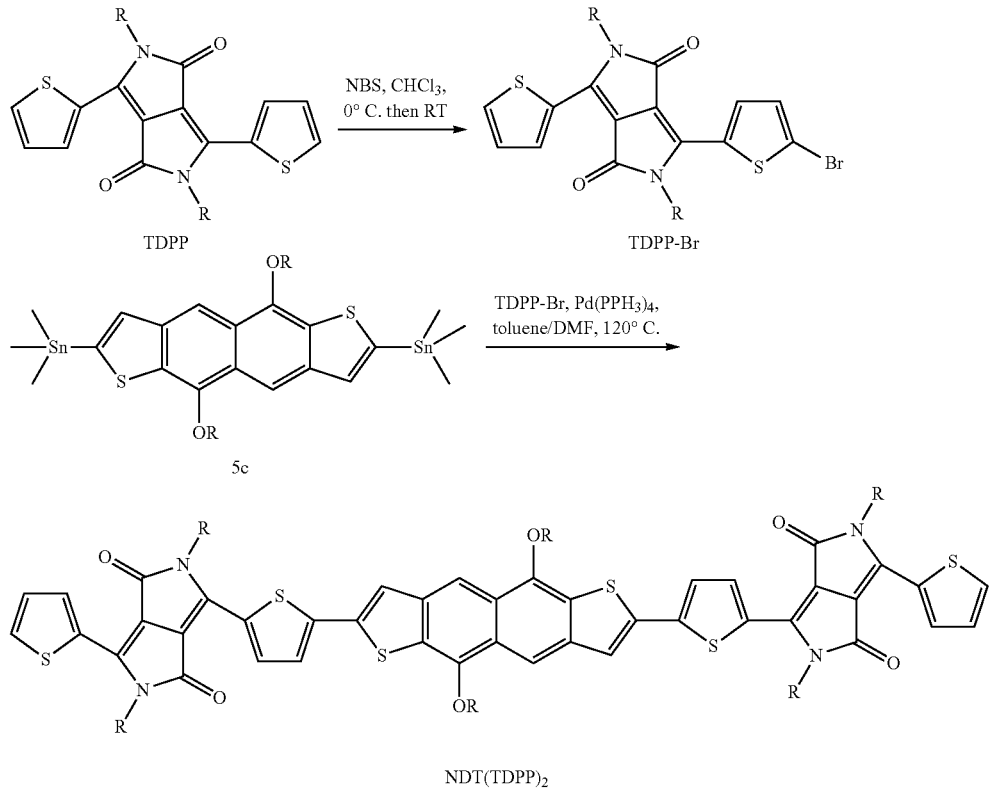

TDPP-Br:

Protected from light, NBS (522 mg, 2.93 mmol) in CHCl$_3$ (50 mL) was added to a solution of TDPP (1.54 g, 2.93 mmol) in CHCl$_3$ (100 mL) at 0° C. over 6 h. The reaction was stirred at ambient temperature overnight and the solvent was removed under reduced pressure. The residue was chromatographed on SiO$_2$ (hexanes—CHCl$_3$, gradient from 9:1 to 3:2) to afford the title compound as a purple solid (934 mg, 53%). $^1$H NMR (500 MHz, CDCl$_3$, 298 K): ∂=8.92 (d, J=3.5 Hz, 1H), 8.65 (d, J=4.0 Hz, 1H), 7.65 (d, J=5.0 Hz, 1H), 7.28 (dd, J=5.0 Hz, 4.0 Hz, 1H), 7.23 (d, J=4.0 Hz, 1H), 4.07-3.90 (m, 4H), 1.90-1.82 (m, 2H), 1.38-1.22 (m, 16H), 0.91-0.82 (m, 8H), 2.02-1.20 (m, 54H), 1.12 (t, J=7.5 Hz, 6H), 1.01 (t, J=7.0 Hz, 6H), 0.97-0.86 (m, 24H) ppm. $^{13}$C NMR (125 MHz, CDCl$_3$, 298 K): ∂=161.6, 161.5, 149.2, 142.1, 140.3, 140.2, 139.3, 136.9, 136.5, 135.5, 130.7, 129.8, 129.6, 128.5, 126.5, 126.4, 125.7, 121.7, 111.3, 108.5, 108.1, 75.6, 45.91, 40.8, 39.3, 39.1, 30.4, 30.4, 30.2, 29.7, 29.2, 28.6, 28.3, 23.9, 23.7, 23.5, 23.2, 23.2, 23.1, 14.3, 14.2, 14.1, 11.4, 10.6, 10.5 ppm. MS (ESI): m/z calcd for C90H117N4O6S6 [M+H]+ 1541.7. found 1541.5. Anal. Calcd for C$_{90}$H$_{116}$N$_4$O$_6$S$_6$: C, 70.09; H, 7.58; N 3.63. Found: C, 70.19; H, 7.55; N, 3.54.

NDT(TDPP)$_2$ optical spectra in chloroform (FIG. 7A) reveal $\lambda_{max}$=624 nm with a very high molar absorption coefficient of $1.1\times10^5$ L·mol$^{-1}$·cm$^{-1}$. A spun cast film from CHCl$_3$ (10 mg·mL$^{-1}$) exhibits a red-shifted $\lambda_{max}$ of 676 nm, suggesting molecular aggregation and coplanarity in the solid state. The absorption onset for the spun cast film is 720 nm, corresponding to an optical band gap of ~1.72 eV. Cyclic voltammetry was used to estimate the HOMO energy. The onset of oxidation at 0.60 V, versus ferrocene/ferrocenium, yields a HOMO energy of −5.40 eV, and from the optical band gap and measured HOMO, the LUMO energy is estimated to be −3.68 eV.

Figure 7:
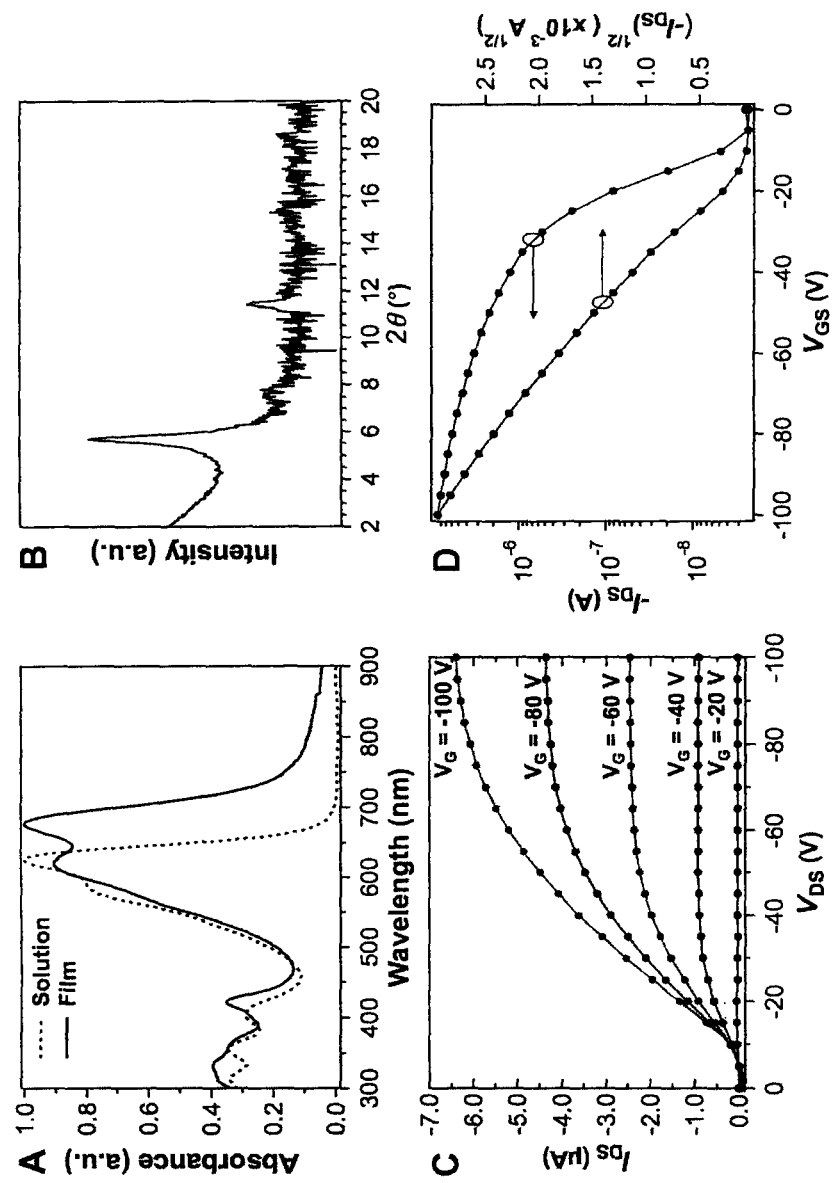
FIG. 7 shows optical absorption spectra (A) of NDT (TDPP)$_2$ in chloroform solution and as a film; (B) log scale θ-2θ X-ray diffraction pattern of a drop cast NDT(TDPP)$_2$ film (from 10 mg·mL$^{-1}$ in chloroform) on a Si/SiO$_2$/HMDS substrate, annealed at 110° C.; (C) typical output and (D) transfer plot ($V_{DS}=-100$V) from a drop cast NDT(TDPP)$_2$ OFET annealed at 110° C.

FIG. 7B shows wide-angle X-ray diffraction (WAXRD) data using standard θ-2θ techniques for a drop cast NDT (TDPP)$_2$ film on a HMDS-treated Si/SiO$_2$ substrate. The reflections at 2θ=5.69° and 11.39° correspond to d-spacings of 15.53 and 7.77 angstroms and indicate long-range order, possibly with edge-on molecular orientation.

Example 7

Fabrication and Characterization of OFETs and OPVs Based on NDT(TDPP)$_2$

Bottom-gate/top-contact OFETs were fabricated on HMDS-treated p-doped Si (001) wafers with 300 nm thermally grown SiO$_2$ as dielectric layer as described in Example 5. The semiconductor layer was deposited by placing 5 drops of NDT(TDPP)$_2$ or NDT(TDPP)$_2$·PC$_{61}$BM (w:w) at 10 mg·mL$^{-1}$ and 20 mg·mL$^{-1}$, respectively, from anhydrous chloroform on an HMDS-treated wafer. After 30 seconds, the remaining solution not dried off was flung off by hand. After the semiconductor was deposited, the device was annealed at 110° C. To complete the device fabrication, 50 nm of Au was thermally evaporated through a shadow mask at ~1×10$^{-6}$ Torr to yield the source and drain electrodes with a channel length and width of 100 and 5000 μm, respectively. Device characterization was carried out in air. Table 3 summarizes the top-contact OFET performance of drop-cast NDT(TDPP)$_2$ and various blend ratios between NDT(TDPP)$_2$ and PC$_{61}$BM on HMDS-treated Si/SiO$_2$ wafer annealed at 110° C., measured in air.

TABLE 3

OFET Device Performances for NDT(TDPP)$_2$ and NDT(TDPP)$_2$·PC$_{61}$BM

| Blend Ratio [D:A] | $\mu_h$ (cm$^2$V$^{-1}$s$^{-1}$) | $V_T$(V) | $I_{on}/I_{off}$ |
|---|---|---|---|
| 2.3:1 | 3 × 10$^{-3}$ | −19.5 | 8 × 10$^2$ |
| 1.5:1 | 3 × 10$^{-3}$ | −19.5 | 5 × 10$^2$ |
| 1:1 | 4 × 10$^{-3}$ | −17.5 | 5 × 10$^2$ |
| NDT(TDPP)$_2$ | 7 × 10$^{-3}$ | −14.9 | 4 × 10$^3$ |

The output and transfer plots of a top-contact OFET from a drop cast NDT(TDPP)$_2$ film on a Si/SiO$_2$/HDMS substrate (FIGS. 7C-7D) indicate p-type behavior with $\mu_h$=7×10$^{-3}$ cm$^2$ V$^{-1}$ s$^{-1}$, among the highest mobilities reported for a solution-processed small-molecule OPV electron donor. OFETs of NDT(TDPP)$_2$PC$_{61}$BM blends exhibit only slightly lower p$_h$ values, suggesting the formation of BHJ domains by the presence of PC$_{61}$BM within the NDT(TDPP)$_2$ network.

OPV devices were fabricated and tested using various blend ratios between NDT(TDPP)$_2$ and PC$_{61}$BM. Patterned ITO-coated glass (Thin Film Device, Inc.), with a resistivity of <10Ω/□ and a thickness of 280 nm was cleaned in sequential sonications at 50° C. in soap/DI water, DI water, methanol, isopropanol, and acetone for 30 min. After the final sonication step, substrates were blown dry with a stream of N$_2$ gas. ITO substrates were then treated for 30 minutes in a UV/O$_3$ oven (Jelight Co.). PEDOT:PSS (Clevios P VP Al 4083) was then spun-cast at 5000 rpm for 30 sec and subsequently annealed at 150° C. for 15 min. Immediately following PEDOT:PSS annealing, samples were blown with a stream of N$_2$ gas to drive off moisture. Samples were then transferred to a N$_2$-filled glove box for active layer and top contact deposition. Active layers containing donor NDT (TDPP)$_2$ and acceptor PC61BM (>99.5% pure, American Dye Source) were formulated inside the glove box in various ratios (w:w) at a total concentration of 20 mg·mL$^{-1}$ in distilled chloroform. Active layer solutions were then allowed to stir at 600-800 rpm for 1.5 h at 40° C. The active layer solutions were spun-cast at 4000 rpm for 15 sec to afford an active layer thickness of ~75 nm (by AFM). Samples were then either thermally annealed at various temperatures (60-150° C.) for 10 min on a temperature-controlled hot plate or left as cast. To finish device fabrication, LiF(1.0 nm)/Al(100 nm) were thermal evaporated, sequentially, at a base pressure of ~4.0×10$^{-6}$ torr. The top Al electrodes were then encapsulated with epoxy and a glass slide before testing. J-V characteristics were measured using the methods stated previously. Each pixel of the device was carefully masked with black rubber to prevent parasitic charge leakage and inaccurate electrode overlap. Each substrate had 4 pixels with a defined area of 0.06 cm$^2$. Table 4 summarizes the J-V and EQE response of various blend ratios between NDT(TDPP)$_2$ and PC$_{61}$BM annealed at 110° C. for 10 minutes.

TABLE 4

J-V and EQE response of OPV devices based on NDT(TDPP)$_2$•PC$_{61}$BM blends

| Blend Ratio [D:A] | $V_{OC}$ [mV] | $J_{SC}$ [mA/cm$^2$] measured | FF (%) | PCE (%) | EQE$_{\lambda-570}$ (%) | $J_{SC}$ [mA/cm$^2$] calculated[a] |
|---|---|---|---|---|---|---|
| 2.3:1 | 870 | 8 | 40 | 2.9 | 45 | 8 |
| 1.5:1 | 840 | 11 | 43 | 4.1 | 66 | 11 |
| 1:1 | 800 | 9 | 38 | 2.9 | 54 | 9 |

[a]Calculated $J_{SC}$ from integrating entire EQE spectrum.

Previous small-molecule bulk-heterojunction (BHJ) solar cells utilizing PC$_{61}$BM as the electron acceptor fullerene have yielded PCEs no higher than 3.7%. The PCE of 4.1% for the NDT(TDPP)$_2$:PC$_{61}$BM (1.5:1, w/w) device reported here is believed to be the highest reported PCE for a PC$_{61}$BM-based small-molecule device and among the highest for any solution-processed small-molecule OPV.

Example 8

Preparation of P(NDT(2EH)-TPD)

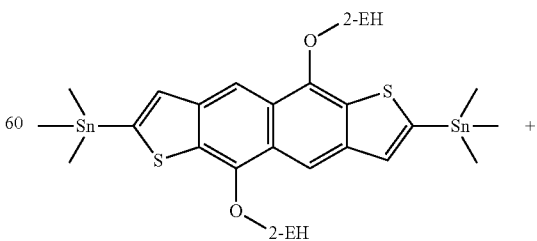

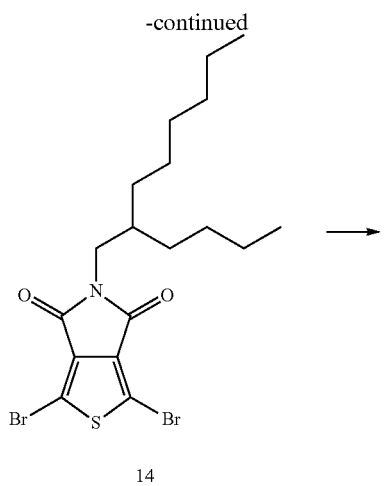

14

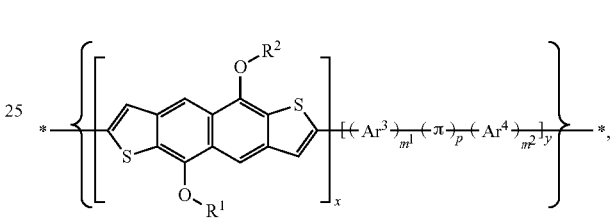

P(NDT(2EH)-TPD)

Compound 14 was synthesized according to the literature procedure (Zou et al., *J. Am. Chem. Soc.* (2010) 132, 5330-5331). Compound 11 (94.0 mg, 0.114 mmol), TPD monomer 14 (54.7 mg, 0.114 mmol), the catalyst Pd(PPh$_3$)$_4$ (13.5 mg, 0.0116 mmol), and toluene (15 ml) were combined under N$_2$ atmosphere and the reaction mixture was stirred at 110° C. for 3 days. 2-Bromothiophene (0.1 ml) was added to the reaction and the reaction was refluxed for 12 hours, then cooled and concentrated in vacuo to the amount of ~1 ml. The concentrated solution was dropped into methanol (100 ml) and the precipitate was then collected via filtration. The black solid was Soxhlet extracted by acetone (1 day), hexane (1 day) and toluene (1 day) in this order. The toluene extract was concentrated and reprecipitation in methanol afforded a dark brown solid (43.1 mg).

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. An electronic, optical or optoelectronic device comprising a polymeric semiconductor component, the polymeric semiconductor component comprising a polymer having formula (I):

$$\left[\left[\begin{array}{c}\text{structure}\end{array}\right]_x \left[(Ar^3)_{m^1}(\pi)_p(Ar^4)_{m^2}\right]_y\right]_*$$

wherein:

R$^1$ and R$^2$ independently are a C$_{1-20}$ alkyl group or a C$_{1-20}$ haloalkyl group;

Ar$^1$ and Ar$^2$ independently are an optionally substituted C$_{6-14}$ aryl group or an optionally substituted 5-14 membered heteroaryl group;

π is an optionally substituted polycyclic aryl or heteroaryl group;

m$^1$ and m$^2$ independently are 0, 1, 2, 3 or 4;

p is 0 or 1;

x and y are real numbers representing mole fractions, wherein 0<x≤1, 0≤y<1, and the sum of x and y is about 1; and the polymer has a degree of polymerization in the range of 5 to 10,000.

2. The device of claim 1, wherein Ar$^1$ and Ar$^2$ independently are an optionally substituted thienyl group or an optionally substituted bicyclic heteroaryl group comprising a thienyl group fused with a 5-membered heteroaryl group.

3. The device of claim 1 or 2, wherein the polymer has the formula:

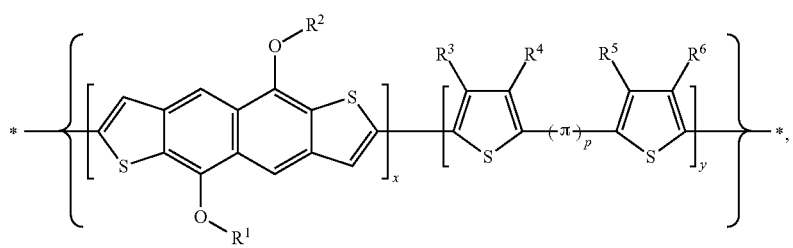

wherein:

R³, R⁴, R⁵, and R⁶ independently are selected from H and R⁷, wherein R⁷, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and R¹, R², π, p, x and y are as defined in claim 1.

4. The device of claim 3, wherein p is 0.

5. The device of claim 1, wherein the polymer has the formula:

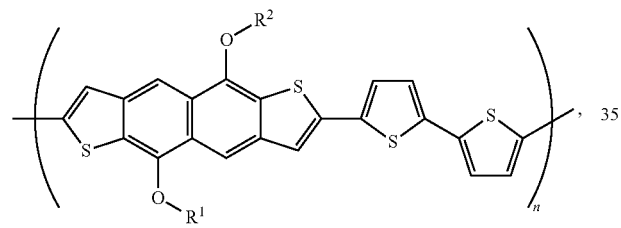

wherein R¹ and R² independently are a $C_{1-20}$ alkyl group, and n is an integer ranging from 5 to 10,000.

6. The device of claim 1, wherein the polymer has the formula:

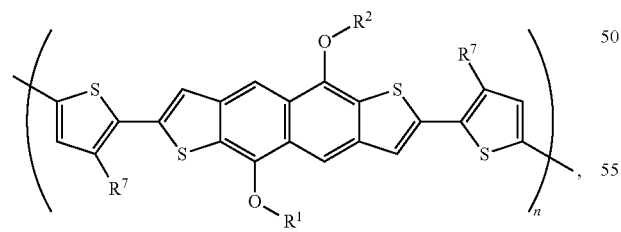

wherein R¹ and R² independently are a $C_{1-20}$ alkyl group, each R⁷ is selected from a halogen, CN, a $C_{1-20}$ alkyl group, a $C_{1-20}$ haloalkyl group, a $C_{1-20}$ alkoxy group, and a $C_{1-20}$ alkylthio group, and n is an integer ranging from 5 to 10,000.

7. The device of claim 1, wherein p is 1.

8. The device of claim 7, wherein each of m¹ and m² is 1.

9. The device of claim 1, wherein the polymer has the formula:

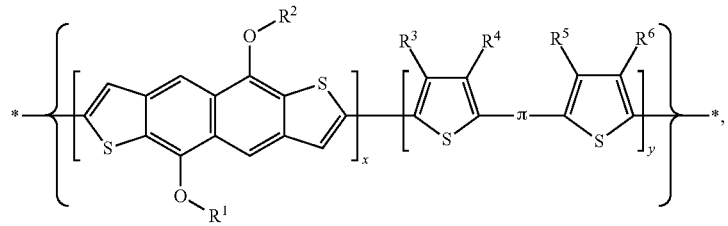

wherein π is an optionally substituted heteroaryl group represented by a formula selected from:

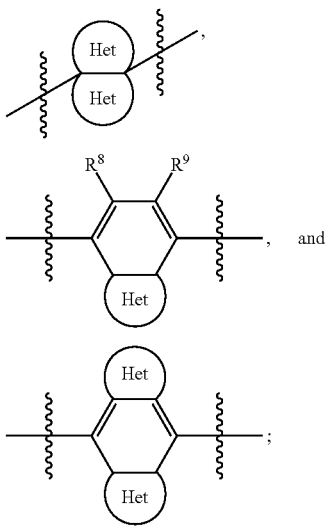

wherein Het, at each occurrence, is a monocyclic moiety including at least one heteroatom in its ring and optionally substituted with 1-2 R¹⁰ groups, wherein R⁸, R⁹, and R¹⁰ independently can be H or R⁷, wherein R⁷, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and R¹, R², R³, R⁴, R⁵, R⁶, x and y are as defined in claim 1.

10. The device of claim 9, wherein π is selected from:

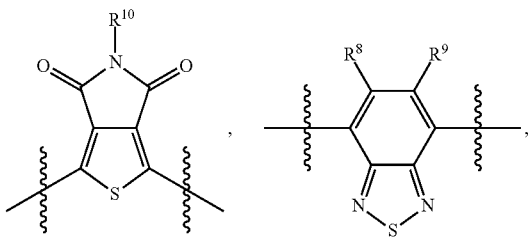

-continued

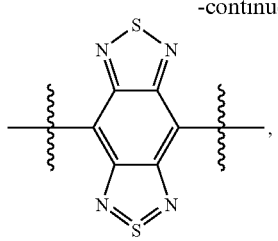

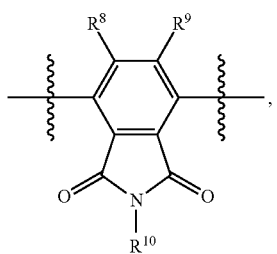

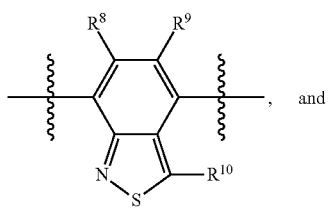, and

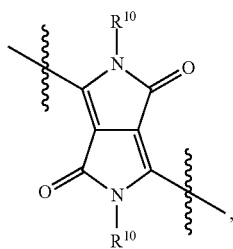, wherein $R^8$, $R^9$, and $R^{10}$ are as defined in claim 9.

11. The device of claim 1, wherein the polymer has the formula:

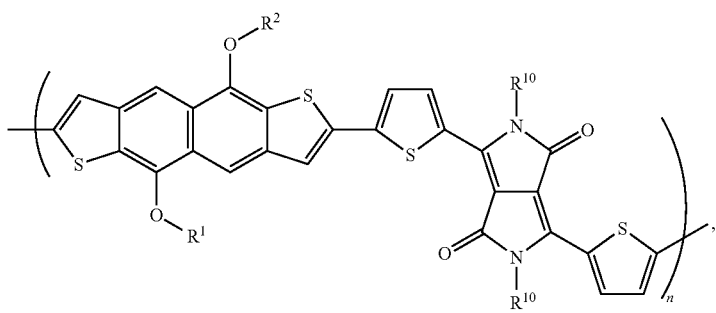

wherein $R^1$, $R^2$ and $R^{10}$ independently are a $C_{1-20}$ alkyl group, and n is an integer ranging from 5 to 10,000.

12. The device of claim 1, wherein the polymer has the formula:

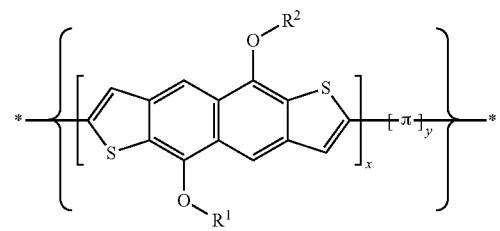

wherein π is an optionally substituted heteroaryl group represented by a formula selected from:

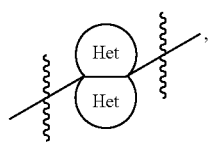,

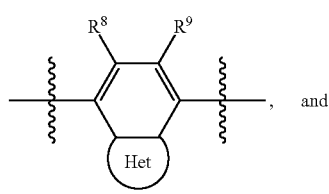, and

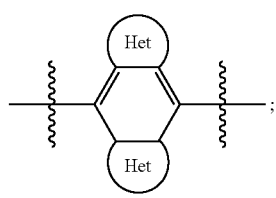;

wherein Het, at each occurrence, is a monocyclic moiety including at least one heteroatom in its ring and optionally substituted with 1-2 $R^{10}$ groups, wherein $R^8$, $R^9$, and $R^{10}$ independently can be H or $R^7$, wherein $R^7$, at each occurrence, independently is selected from a halogen, CN, a $C_{1-20}$ alkyl group, a $C_{1-20}$ haloalkyl group, a $C_{1-20}$ alkoxy group, and a $C_{1-20}$ alkylthio group; and $R^1$, $R^2$, x and y are as defined in claim 1.

13. The device of claim 1, wherein the polymer has the formula:

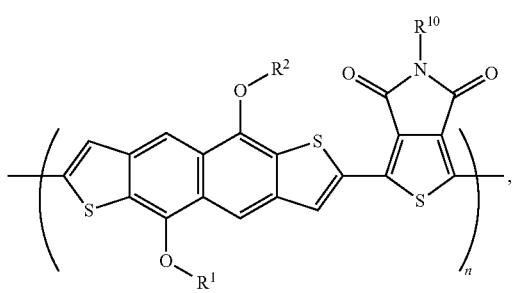

wherein $R^1$, $R^2$ and $R^{10}$ independently are a $C_{1-20}$ alkyl group, and n is an integer ranging from 5 to 10,000.

14. A polymer having formula (I):

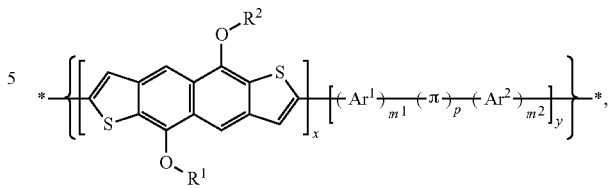

wherein:
$R^1$ and $R^2$ independently are a $C_{1-20}$ alkyl group or a $C_{1-20}$ haloalkyl group;
$Ar^1$ and $Ar^2$ independently are an optionally substituted $C_{6-14}$ aryl group or an optionally substituted 5-14 membered heteroaryl group;
π is an optionally substituted polycyclic aryl or heteroaryl group;
$m^1$ and $m^2$ independently are 0, 1, 2, 3 or 4;
p is 0 or 1;
x and y are real numbers representing mole fractions, wherein $0<x\leq1$, $0\leq y<1$, and the sum of x and y is about 1; and
the polymer has a degree of polymerization in the range of 5 to 10,000.

* * * * *